(12) United States Patent
De Luca et al.

(10) Patent No.: US 11,274,133 B2
(45) Date of Patent: *Mar. 15, 2022

(54) IL2 AND TNF IMMUNOCONJUGATES

(71) Applicant: PHILOGEN S.P.A., Siena (IT)

(72) Inventors: Roberto De Luca, Rivera (CH); Francesca Pretto, Zurich (CH); Sarah Wulhfard, Neuenhof (CH)

(73) Assignee: PHILOGEN S.P.A., Siena (IT)

( * ) Notice: Subject to any disclaimer, the term of this patent is extended or adjusted under 35 U.S.C. 154(b) by 434 days.

This patent is subject to a terminal disclaimer.

(21) Appl. No.: 16/383,444

(22) Filed: Apr. 12, 2019

(65) Prior Publication Data

US 2019/0284253 A1 Sep. 19, 2019

Related U.S. Application Data

(63) Continuation of application No. 15/564,694, filed as application No. PCT/EP2016/060128 on May 5, 2016, now Pat. No. 10,308,696.

(30) Foreign Application Priority Data

May 8, 2015 (GB) .................................... 1507908

(51) Int. Cl.
| | |
|---|---|
| *C07K 14/525* | (2006.01) |
| *C07K 14/55* | (2006.01) |
| *C07K 16/18* | (2006.01) |
| *A61K 47/68* | (2017.01) |
| *A61P 35/00* | (2006.01) |
| *A61K 38/00* | (2006.01) |

(52) U.S. Cl.
CPC ........ *C07K 14/525* (2013.01); *A61K 47/6813* (2017.08); *A61K 47/6851* (2017.08); *A61P 35/00* (2018.01); *C07K 14/55* (2013.01); *C07K 16/18* (2013.01); *A61K 38/00* (2013.01); *C07K 2317/622* (2013.01); *C07K 2317/73* (2013.01); *C07K 2319/33* (2013.01); *C07K 2319/74* (2013.01); *C07K 2319/75* (2013.01)

(58) Field of Classification Search
None
See application file for complete search history.

(56) References Cited

FOREIGN PATENT DOCUMENTS

| | | |
|---|---|---|
| EP | 0580859 A1 | 2/1994 |
| EP | 2142567 B1 | 1/2013 |
| EP | 2209805 B1 | 9/2017 |
| WO | WO 2014/055073 A1 | 4/2014 |
| WO | WO 2015/088348 A1 | 6/2015 |

OTHER PUBLICATIONS

De Luca et al., "Potency-matched Dual Cytokine-Antibody Fusion Proteins for Cancer Therapy", Molecular Cancer Therapeutics, 2017, 16(11): 2442-2451.
Pretto et al., "Preclinical evaluation of IL2-based immunocytokines supports their use in combination with dacarbazine, paclitaxel and TNF-based immunotherapy", Cancer Immunology Immunotherapy, 2014, 63:901-910.
Halin et al., "Synergistic Therapeutic Effects of a Tumor Targeting Antibody Fragment, Fused to Interleukin 12 and to Tumor Necrosis Factor α1", Cancer Research 2003, 63: 3202-3210.
Schwager et al., "The Immunocytokine L19-IL2 Eradicates Cancer When Used in Combination with CTLA-4 Blockade or with L19-TNF", Journal of Investigative Dermatology, 2013, 133: 751-758.
Hemmerle et al., "Tumor targeting properties of antibody fusion proteins based on different members of the murine tumor necrosis superfamily", Journal of Biotechnology, 2014, 172:73-76.
List et al., "Immunocytokines: a review of molecules in clinical development for cancer therapy", Clinical Pharmacology: Advances and Applications, 2013, 5(Suppl 1):29-45.
Pasche et al., "Immunocytokines: a novel class of potent armed antibodies", Drug Discovery, 2012, 17(11/12): 583-590.
List et al., "A Chemically Defined Trifunctional Antibody—Cytokine—Drug Conjugate with Potent Antitumor Activity", Molecular Cancer Therapeutics, 2014, 13(11): 2641-2652.
Bootz et al., "Immunocytokines: a novel class of products for the treatment of chronic inflammation and autoimmune conditions", Drug Discovery Today, 2016, 21(1):180-189.
Danielli et al., "Intralesional administration of L19-IL2/L19-TNF in stage III or stage IVM1a melanoma patients: results of a phase II study", Cancer Immunology Immunotherapy, 2015, 64:999-1009.
Borsi et al., "Monoclonal Antibodies in the Analysis of Fibronectin Isoforms Generated by Alternative Splicing of mRNA Precursors in Normal and Transformed Human Cells", The Journal of Cell Biology, 1987, 104: 595-600.
Borsi et al., "Preparation of Phage Antibodies to the ED-A Domain of Human Fibronectin", Experimental Cell Research, 1998, 240: 244-251.
Burton-Wurster et al., "Molecular and Immunologic Differences in Canine Fibronectins from Articular Cartilage and Plasma", Archives of Biochemistry and Biophysics, 1989, 269(1): 32-45.
Carnemolla et al., "Localization of the cellular-fibronectin-specific epitope recognized by the monoclonal antibody IST-9 using fusion proteins expressed in *E. coli*", FEBS Letters, 1987, 215(2): 269-273.
Liao et al., "Identification of Two Amino Acids within the EIIIA (ED-A) Segment of Fibronectin Constituting the Epitope for Two Function-blocking Monoclonal Antibodies", The Journal of Biological Chemistry, 1999, 274(25): 17876-17884.
Meerschaert et al., "Segmental Antigen Challenge Increases Fibronectin in Bronchoalveolar Lavage Fluid", Am J Respir Crit Care Med, 1999, 159: 619-625.
Moore et al., "Fibronectin-α4β1 Integrin Interactions Regulate Metalloproteinase-9 Expression in Steatotic Liver Ischemia and Reperfusion Injury", The American Journal of Pathology, 2007, 170(2): 567-577.

(Continued)

*Primary Examiner* — Daniel C Gamett
(74) *Attorney, Agent, or Firm* — James S. Keddie; Bozicevic, Field & Francis LLP

(57) ABSTRACT

The present application relates to conjugates comprising interleukin 2 (IL2), and a tumour necrosis factor, such as tumour necrosis factor alpha (TNFα), and an antibody molecule. The antibody molecule preferably binds to an antigen associated with neoplastic growth and/or angiogenesis, such as the Extra-Domain A (EDA) of fibronectin. The conjugate may be used in the treatment of cancer.

18 Claims, 8 Drawing Sheets

Specification includes a Sequence Listing.

(56) References Cited

OTHER PUBLICATIONS

Ou et al., "Fibronectin Extra Domain A (EDA) Sustains CD133+/CD44+ Subpopulation of Colorectal Cancer Cells", Stem Cell Res., 2013, 11(2): 820-833. doi:10.1016/j.scr.2013.05.009.
Oyama et al, "Coordinate Oncodevelopmental Modulation of Alternative Splicing of Fibronectin Pre-Messenger RNA at ED-A, ED-B, and CS1 Regions in Human Liver Tumors", Cancer Research, 1993, 53: 2005-2011.
Salcedo et al., "Endogenous Fibronectin of Blood Polymorphonuclear Leukocytes: Immunochemical Characterization and Subcellular Localization", Experimental Cell Research, 1997, 233: 25-32.
Serini et al., "The Fibronectin Domain ED-A Is Crucial for Myofibroblastic Phenotype Induction by Transforming Growth Factor-$\beta$1", The Journal of Cell Biology, 1998, 142(3): 1873-881.
Shinde et al., "Identification of the Peptide Sequences within the EIIIA (EDA) Segment of Fibronectin That Mediate Integrin $\alpha 9\beta 1$-dependent Cellular Activities", The Journal of Biological Chemistry, 2008, 283(5): 2858-2870.
Tan et al., "Deletion of the alternatively spliced fibronectin EIIIA domain in mice reduces atherosclerosis", Blood, 2004, 104(1): 11-18.
Villa et al., "A high-affinity human monoclonal antibody specific to the alternatively spliced EDA domain of fibronectin efficiently targets tumor neo-vasculature in vivo", Int. J. Cancer, 2008, 122: 2405-2413.

A

B

IL2 AND TNF IMMUNOCONJUGATES

Cross-Reference to Related Applications

This application is a continuation of U.S. Application Ser. No. 15/564,694, filed on Oct. 5, 2017, which is a § 371 national phase of International Application No. PCT/EP2016/060128, filed on May 5, 2016, which claims the benefit of United Kingdom Application No. 1507908.0, filed on May 8, 2015, which applications are incorporated by reference herein.

FIELD OF THE INVENTION

The present invention relates to conjugates comprising interleukin 2 (IL2), and a tumour necrosis factor, such as tumour necrosis factor alpha (TNFα), and an antibody molecule. The antibody molecule preferably binds to an antigen associated with neoplastic growth and/or angiogenesis, such as the Extra-Domain A (EDA) of fibronectin. The conjugate may be used in the treatment of cancer.

BACKGROUND TO THE INVENTION

Many cytokines have shown potent antitumor activities in preclinical experiments and represent promising agents for cancer therapy. However, despite encouraging results in animal models, only a few cytokines, such as Proleukin 1 (IL2), Roferon A1 (interferon alpha-2a [IFNα 2a]), Intron A1 (IFNα 2b), Beromun 1 (recombinant TNFα) are approved as anticancer drugs. Current indications for cytokines include metastatic renal cell cancer, malignant melanoma, hairy cell leukemia, chronic myeloid lymphoma, sarcoma and multiple myeloma. The cytokines may be either administered alone or in combination with chemotherapy.

A further difficulty with pro-inflammatory cytokines in particular is that their use in therapy is often hindered by substantial toxicity even at low doses, which prevents the escalation to therapeutically active doses (Hemmerle et al. (2013) *Br. J. Cancer* 109, 1206-1213).

In an attempt to increase the therapeutic index of certain cytokines, antibody-cytokine fusion proteins (also referred to as "immunocytokines") have been proposed. In these conjugates, the antibody serves as a "vehicle" for a selective accumulation at the site of disease, while the cytokine payload is responsible for the therapeutic activity (Pasche & Neri, 2012, Drug Discov. Today, 17, 583). Certain immunocytokines based on pro-inflammatory payloads (such as IL2, IL4, IL12, and TNFα) display potent anti-cancer activity in mouse models (Hess et al., 2014, Med. Chem. Comm., 5, 408) and have produced encouraging results in patients with both solid tumours and hematological malignancies (Eigentler et al., 2011, Clin. Cancer Res. 17, 7732-7742; Papadia et al., 2013, J. Surg. Oncol. 107, 173-179; Gutbrodt et al., 2013, Sci. Transl. Med. 5, 201-204; Weide et al., 2014, *Cancer Immunol. Res.* 2, 668-678; Danielli et al., 2015, Cancer Immunol. Immunother. 64, 113-121]. The F8 antibody (specific to the alternatively-spliced EDA domain of fibronectin, a marker of tumor angiogenesis; Rybak et al. (2007) Cancer Res. 67, 10948-10957) has been used for tumor targeting, both alone and fused to either TNF or IL2 (Villa et al. (2008) *Int. J. Cancer* 122, 2405-2413; Hemmerle et al. (2013) *Br. J. Cancer* 109, 1206-1213; Frey et al. (2008) *J. Urol.* 184, 2540-2548).

In some cases, immunocytokines can mediate tumor eradication in mouse models of cancer when used as single agents (Gutbrodt et al., 2013, Sci. Transl. Med. 5, 201-204]. In most cases, however, a single immunocytokine product is not able to induce complete cancer eradication. However, cancer cures have been reported for combinations of immunocytokines with cytotoxic agents (Moschetta et al., 2012, Cancer Res. 72, 1814-1824], intact antibodies (Schliemann et al., 2009, Blood, 113, 2275-2283] and external beam radiation (Zegers et al., 2015, Clin. Cancer Res., 21, 1151-1160).

In addition, several combinations of immunocytokines have been used in therapy. For example, conjugates L19-IL2 and L19-TNFα were able to cure neuroblastoma in a fully syngeneic mouse model of the disease, whereas the individual immunocytokines used as single agents did not result in eradication of the disease (Balza et al., 2010, Int. J. Cancer, 127, 101). The combination of IL2 and TNFα payloads has also shown promising results in clinical trials. The fusion proteins L19-IL2 and L19-TNF were shown to potently synergize for the intralesional treatment of certain solid tumors in the mouse (Schwager et al., 2013, J. Invest. Dermatol. 133, 751-758). The corresponding fully human fusion proteins have been administered intralesionally to patients with Stage IIIC melanoma (Danielli et al., 2015, Cancer Immunol. Immunother. 64, 113-121), showing better results compared to the intralesional administration of interleukin-2 (Weide et al., 2011, Cancer—116, 4139-4146) or of L19-IL2 (Weide et al., 2014, Cancer Immunol. Immunother. 2, 668-678). However, the genetic fusion of a cytokine to an antibody does not always result in increased efficacy. For example, the fusion of Interleukin-17 to a targeting antibody did not reduce tumour growth (Pasche et al., 2012, Angiogenesis 15, 165-169).

There have also been attempts to generate "dual immunocytokines" in which an antibody is genetically fused to two different cytokines. For instance interleukin-12 (IL12) and TNFα have been incorporated into a single molecular entity. However, these attempts have not been successful and have not led to clinical development programs.

Specifically, a triple fusion, consisting of: (i) the L19 antibody in scFv format (specific to the alternatively-spliced EDB domain of fibronectin, a marker of tumor angiogenesis); (ii) murine TNFα; and (iii) murine IL12 in single-chain format has been described (Halin et al., 2003, Cancer Res., 63, 3202-3210). The fusion protein could be expressed and purified to homogeneity. The fusion protein also bound to the cognate antigen with high affinity and specificity, but (unlike L19-TNFα and L19-IL12) failed to localize to solid tumors in vivo, as evidenced by quantitative biodistribution studies in tumor-bearing mice.

Bi-functional cytokine fusion proteins in which the cytokines were linked to an intact antibody (or the Fc portion of an antibody) have also been described. These fusion proteins comprised interleukin-2/interleukin-12 (IL-2/IL-12), or interleukin-4/granulocyte-macrophage colony-stimulating factor (IL-4/GM-CSF). Cytokine activity was retained in constructs where the cytokines were fused in tandem at the carboxyl terminus of the Fc or antibody heavy (H) chain, as well as in constructs where one cytokine was fused at the carboxyl terminus of the H chain while the second cytokine was fused to the amino terminus of either the H or light (L) chain variable region. Antigen binding of the antibody-cytokine fusion proteins was maintained. However, therapeutic activities in vivo were reported only for gene therapy applications (i.e., tumor cells transfected with the appropriate IL2/IL12 immunocytokines), but not with therapeutic proteins (Gillies et al., 2002, Cancer Immunol. Immunother., 51, 449).

As a result of the intrinsic complexity of successfully expressing immunoconjugates comprising two cytokines in a single molecule (also referred to as "dual immunocytokines"), as well as the unpromising results obtained with such molecules as discussed above, these molecular formats have not been pursued for clinical applications.

STATEMENTS OF INVENTION

The present inventors have prepared a conjugate comprising the F8 antibody, which is specific for the Extra-Domain A (EDA) of fibronectin, in scFv format, IL2 and TNFα. This conjugate not only has advantages with respect to manufacturing and administration over the use of two separate conjugates, comprising 1L2 and TNFα, respectively, but surprisingly shows improved tumour targeting in vivo compared with conjugates comprising the same antibody and either IL2 or TNFα. This was particularly unexpected given the lack of tumour targeting observed with an immunocytokine comprising TN Fa and IL12 as disclosed in Halin et al. (2003) and lack of therapeutic activity reported for immunocytokines comprising IL-2 and IL-12 or IL-4 and GM-CSF in Gillies et al. (2002).

Furthermore the present inventors found that when administered to tumor bearing mice, the new conjugate retains the in vivo therapeutic activity seen in mice with combined administration of (i) the F8 antibody conjugated to TNFα and (ii) the F8 antibody conjugated to IL2, while surprisingly having a remarkably milder toxicity profile.

Thus, in the present invention relates to a conjugate comprising interleukin-2 (IL2), a tumor necrosis factor, preferably TNFα, and an antibody molecule which binds an antigen associated with neoplastic growth and/or angiogenesis. The present invention also relates to a nucleic acid molecule encoding such a conjugate, as well as an expression vector comprising such a nucleic acid. A host cell comprising such a vector is also contemplated.

The present invention also relates to a conjugate of the invention for use in a method of treating cancer by targeting IL2 and a tumor necrosis factor, preferably TNFα, to the neovasculature in vivo, as well as a conjugate according to the invention for use in a method of delivering IL2 and a tumor necrosis factor, preferably TNFα, to the tumour neovasculature in a patient.

The present invention further relates to a method of treating cancer by targeting IL2 and a tumor necrosis factor, preferably TNFα, to the neovasculature in a patient, the method comprising administering a therapeutically effective amount of a conjugate of the invention to the patient, as well as a method of delivering IL2 and a tumor necrosis factor, preferably TNFα, to the tumour neovasculature in a patient comprising administering to the patient a conjugate according to the present invention.

In addition, the present invention relates to the use of a conjugate of the invention for the preparation of a medicament for the treatment of cancer. The use of a conjugate of the invention for the preparation of a medicament for delivery of IL2 and a tumor necrosis factor, preferably TNFα, to the neovasculature of a tumour is similarly contemplated.

BRIEF DESCRIPTION OF THE FIGURES

FIG. 7 demonstrates that the cell killing activity of the different conjugate formats was comparable, as there was not statistically significant difference between the activities observed for the different conjugate formats tested.

Figure 1:
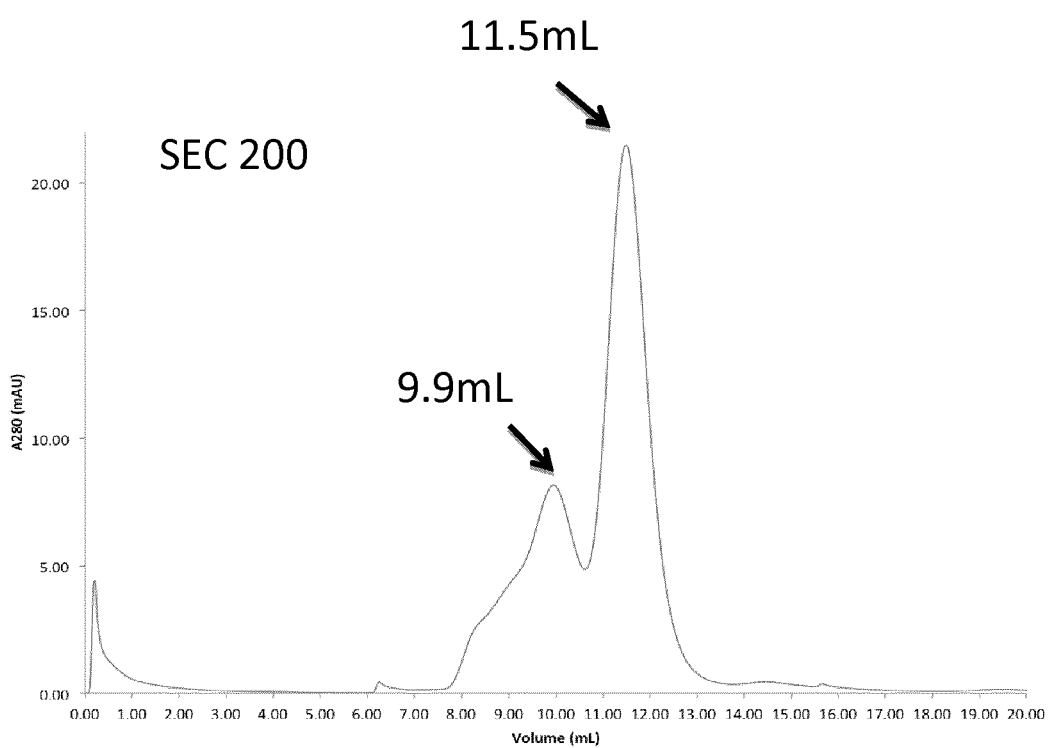
FIG. 1 shows the results of Size Exclusion Chromatography of the purified muIL2-F8-muTNFα conjugate. The peak with retention volume 11.5 mL corresponds to a trimeric fraction of the conjugate. The peak at a retention volume of 9.9 mL represents a non-covalent-multimeric species of the conjugate.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

DETAILED DESCRIPTION

Antibody Molecule

This describes an immunoglobulin whether natural or partly or wholly synthetically produced. The term also relates to any polypeptide or protein comprising an antibody antigen-binding site. It must be understood here that the antibody molecules may have been isolated or obtained by purification from natural sources, or else obtained by genetic recombination, or by chemical synthesis, and that they can contain unnatural amino acids.

As antibodies can be modified in a number of ways, the term "antibody molecule" should be construed as covering any specific binding member or substance having an antibody antigen-binding site with the required specificity and/or binding to antigen. Thus, this term covers antibody fragments, in particular antigen-binding fragments, and derivatives, including any polypeptide comprising an antibody antigen-binding site, whether natural or wholly or partially synthetic. Chimeric molecules comprising an antibody antigen-binding site, or equivalent, fused to another polypeptide (e.g. belonging to another antibody class or subclass) are therefore included. Cloning and expression of chimeric antibodies are described in EP-A-0120694 and EP-A-0125023, and a large body of subsequent literature.

As mentioned above, fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al. (1989) Nature 341, 544-546; McCafferty et al., (1990) Nature, 348, 552-554; Holt et al. (2003) Trends in Biotechnology 21, 484-490), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al. (1988) Science, 242, 423-426; Huston et al. (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger et al. (1993a), Proc. Natl. Acad. Sci. USA 90 6444-6448). Fv, scFv or diabody molecules may be stabilized by the incorporation of disulphide bridges linking the VH and VL domains (Reiter et al. (1996), Nature Biotech, 14, 1239-1245). Minibodies comprising a scFv joined to a CH3 domain may also be made (Hu et al. (1996), Cancer Res., 56(13):3055-61). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

The half-life of antibody molecules for use in the present invention, or conjugates of the invention, may be increased by a chemical modification, especially by PEGylation, or by incorporation in a liposome.

An antibody molecule for use in the present invention preferably is, or comprises, an scFv. An antibody which comprises an scFv includes a diabody. Most preferably, the antibody molecule for use in the present invention is an scFv. Diabodies and scFvs do not comprise an antibody Fc region, thus potentially reducing the effects of anti-idiotypic reaction.

Where the antibody molecule is an scFv, the VH and VL domains of the antibody are preferably linked by a 14 to 20 amino acid linker. Suitable linkers are known in the art and available to the skilled person. For example, the linker may have the sequence set forth in SEQ ID NO: 3.

Where the antibody molecule is a diabody, the VH and VL domains may be linked by a 5 to 12 amino acid linker. A diabody comprises two VH-VL molecules which associate to form a dimer. The VH and VL domains of each VH-VL molecule may be linked by a 5 to 12 amino acid linker.

The present inventors have shown that a conjugate comprising IL2 and TNFα and an antibody molecule which binds the Extra-Domain A (ED-A) of fibronectin can successfully target tumour neovasculature in vivo. It is expected that other conjugates comprising IL2 and a tumour necrosis factor, preferably TNFα, and an antibody molecule which binds an antigen associated with neoplastic growth and/or angiogenesis will similarly be suitable to target IL2 and TNF to the tumour neovasculature and thus find application in cancer treatment. Many such antigens are known in the art, as are antibodies capable of binding such antigens. In additions, antibodies against a given antigen can be generated using well-known methods such as those described in the present application. In one example, the antigen may be an extra-cellular matrix component associated with neoplastic growth and/or angiogenesis, such as fibronectins, including the Extra-Domain A (ED-A) isoform of fibronectin (A-FN), the Extra-Domain B (ED-B) isoform of fibronectin (B-FN), tenascin C, the ED-A of fibronectin, the ED-B of fibronectin, or the A1 Domain of Tenascin C. Antibodies which bind the ED-A of fibronectin, and thus also A-FN, are known in the art and include antibody F8. Antibodies which bind the ED-B of fibronectin, or the A1 Domain of Tenascin C (and thus also the B-FN and tenascin C) are also known in the art and include antibodies L19 and F16, respectively. Antibodies which bind the ED-B of fibronectin, or the A1 Domain of Tenascin C, including antibodies L19 and F16, have been shown to be capable of specifically targeting the tumour neovasculature in vivo. It is thus expected that conjugates comprising IL2 and a tumour necrosis factor, preferably TNFα, and an antibody molecule which binds B-FN, tenascin C, the ED-B of fibronectin, or the A1 Domain of Tenascin C, will be capable of targeting IL2 and TNF to the tumour neovasculature, in the same way as a conjugate comprising IL2 and TNF and an antibody molecule which binds A-FN, as demonstrated using antibody F8 herein and thus find application in cancer treatment. Other antigens which are associated with neoplastic growth and/or angiogenesis include carbonic anhydrase IX (a marker of renal cell carcinoma), A33 and CEA (good markers of colorectal cancer), HER2 (a marker of breast cancer), PSMA (a marker of prostate cancer) and fibroblast activation protein (a protease, present both as membrane bound protein and as shed protein, on activated fibroblasts and on certain types of tumor cells). Again, it is expected that conjugates comprising IL2 and a tumour necrosis factor, preferably TNFα, and an antibody molecule which binds antigens such as carbonic anhydrase IX, A33, CEA, HER2, PSMA, or fibroblast activation protein will similarly be suitable to target IL2 and TNF to the tumour neovasculature and thus find application in cancer treatment.

Thus an antibody molecule for use in the invention may bind an antigen associated with neoplastic growth and/or angiogenesis. Preferably, antibody molecule for use in the invention binds an extra-cellular matrix component associated with neoplastic growth and/or angiogenesis, such as A-FN, B-FN, tenascin C, the ED-A of fibronectin, the ED-B of fibronectin, or the A1 Domain of Tenascin C. More preferably, an antibody molecule for use in the invention binds the A-FN or the ED-A of fibronectin. Most preferably, an antibody molecule for use in the invention binds the ED-A of fibronectin. Alternatively, an antibody molecule for use in the invention may bind carbonic anhydrase IX, A33, CEA, HER2, PSMA, or fibroblast activation protein. Antibody molecules which bind these antigens are known in the art.

The present inventors have also shown that a conjugate comprising IL2 and TNFα and an antibody molecule which binds the Extra-Domain A (ED-A) of fibronectin exhibits reduced toxicity compared than combined administration of (i) the anti-EDA antibody conjugated to TNFα and (ii) the anti-EDA antibody conjugated to IL2. It is expected that other conjugates comprising IL2 and a tumour necrosis factor, preferably TNFα, and an antibody molecule which binds an antigen associated with neoplastic growth and/or angiogenesis will similarly have reduced toxicity. Thus, a conjugate according to the present invention, comprising IL2, TNFα, and an antibody molecule which binds an antigen associated with neoplastic growth and/or angiogenesis, preferably exhibits reduced toxicity when administered to a patient, compared with combined administration of (i) a conjugate comprising the antibody molecule and TNFα, and (ii) a conjugate comprising the antibody molecule and IL2, to the patient. Reduced Toxicity may refer to a reduction in one or more adverse symptoms associated with administration of the conjugate(s) to a patient. Such adverse symptoms may include weight loss, nausea, vomiting, fever, chills, flushing, urticaria, rash, pulmonary toxicity, dyspnea, hypotension, anaphylaxis, serum sickness, increased creatinine, headache.

In a preferred embodiment, an antibody molecule for use in the invention may have the CDRs and/or the VH and/or VL domains of antibodies F8, L19 or F16 described herein. An antibody molecule for use in the invention preferably has the CDRs of antibody F8 set forth in SEQ ID NOs 6-11. More preferably, an antibody for use in the invention comprises the VH and/or VL domains of antibody F8 set forth in SEQ ID NOs 2 and 4. Yet more preferably, an antibody for use in the invention comprises the VH and VL domains of antibody F8 set forth in SEQ ID NOs 2 and 4. The F8 antibody is preferably in scFv or diabody format, most preferably in scFv format. Where the F8 antibody is in scFv format, the antibody molecule for use in the invention preferably has the amino acid sequence set forth in SEQ ID NO: 5.

An antibody for use in the invention may bind the A-FN and/or the ED-A of fibronectin, with the same affinity as anti-ED-A antibody F8 e.g. in scFv format, or with an affinity that is better. An antibody molecule for use in the invention may bind the B-FN and/or the ED-B of fibronectin, with the same affinity as anti-ED-B antibody L19 e.g. in scFv format, or with an affinity that is better. An antibody molecule for use in the invention may bind the Tenascin C and/or the A1 domain of tenascin C, with the same affinity as anti-ED-A antibody F16 e.g. in scFv format, or with an affinity that is better.

An antibody molecule of the present invention may bind to the same epitope on A-FN and/or the ED-A of fibronectin as anti-ED-A antibody F8. An antibody molecule of the present invention may bind to the same epitope on B-FN and/or the ED-B of fibronectin as anti-ED-A antibody L19. An antibody molecule of the present invention may bind to the same epitope on tenascin C and/or the A1 domain of tenascin C as antibody F16.

Variants of antibody molecules disclosed herein may be produced and used in the present invention. The techniques required to make substitutions within amino acid sequences of CDRs, antibody VH or VL domains, in particular the framework regions of the VH and VL domains, and antibody molecules generally are available in the art. Variant sequences may be made, with substitutions that may or may not be predicted to have a minimal or beneficial effect on activity, and tested for ability to bind A-FN and/or the ED-A of fibronectin, B-FN and/or the ED-B of fibronectin, tenascin C and/or the A1 domain of tenascin C, and/or for any other desired property.

It is contemplated that from 1 to 5, e.g. from 1 to 4, including 1 to 3, or 1 or 2, or 3 or 4, amino acid alterations (addition, deletion, substitution and/or insertion of an amino acid residue) may be made in one or more of the CDRs and/or the VH and/or the VL domain of an antibody molecule as described herein. Thus, an antibody molecule which binds the FN-A, FN-B, or tenascin C, may comprise the CDRs and/or the VH and/or the VL domain of antibody F8, L19, or F16 described herein with 5 or fewer, for example, 5, 4, 3, 2 or 1 amino acid alterations within the CDRs and/or the VH and/or the VL domain. For example, an antibody molecule which binds the FN-A, FN-B, or tenascin C, may comprise the VH and/or the VL domain of antibody F8, L19, or F16 described herein with 5 or fewer, for example, 5, 4, 3, 2 or 1 amino acid alterations within the framework region of the VH and/or VL domain. An antibody molecule that binds the FN-A or ED-A of fibronectin, as referred to herein, thus may comprise the VH domain shown in SEQ ID NO: 2 and/or the VL domain shown in SEQ ID NO: 4 with 5 or fewer, for example, 5, 4, 3, 2 or 1 amino acid alterations within the framework region of the VH and/or VL domain. Such an antibody molecule may bind the ED-A isoform or ED-A of fibronectin with the same or substantially the same, affinity as an antibody molecule comprising the VH domain shown in SEQ ID NO: 2 and the VL domain shown in SEQ ID NO: 4 or may bind the ED-A isoform or ED-A of fibronectin with a higher affinity than an antibody molecule comprising the VH domain shown in SEQ ID NO: 2 and the VL domain shown in SEQ ID NO: 4.

An antibody molecule for use in the invention may comprise a VH and/or VL domain that has at least 70%, more preferably one of at least 75%, 80%, 85%, 90%, 95%, 96%, 97%, 98%, 99% or 100%, sequence identity to the VH and/or VL domain, as applicable, of antibody F8, L19, or F16 set forth in SEQ ID NOs 2, 4, 27, 28, 36, and 37. An antibody molecule for use in the invention may have at least 70%, more preferably one of at least 75%, 80%, 85%, 90%, 95%, 96%, 97%, 98%, 99% or 100%, sequence identity to the amino acid sequence of the F8, L19, or F16 antibodies set forth in SEQ ID NOs 5, 29, and 38, respectively.

Antigen-Binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site preferably comprises an antibody light chain variable region (VL) and an antibody heavy chain variable region (VH).

An antigen binding site may be provided by means of arrangement of complementarity determining regions (CDRs). The structure for carrying a CDR or a set of CDRs will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat et al. (1987) (Sequences of Proteins of Immunological Interest. $4^{th}$ Edition. US Department of Health and Human Services.), and updates thereof, now available on the Internet (at immuno.bme.nwu.edu or find "Kabat" using any search engine).

By CDR region or CDR, it is intended to indicate the hypervariable regions of the heavy and light chains of the immunoglobulin as defined by Kabat et al. (1987) Sequences of Proteins of Immunological Interest, $4^{th}$ Edition, US Department of Health and Human Services (Kabat et al., (1991a), Sequences of Proteins of Immunological Interest, $5^{th}$ Edition, US Department of Health and Human Services, Public Service, NIH, Washington, and later editions). An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It can be as short as 2 amino acids although the longest size known is 26. Functionally, HCDR3 plays a role in part in the determination of the specificity of the antibody (Segal et al., (1974), PNAS, 71:4298-4302; Amit et al., (1986), Science, 233:747-753; Chothia et al., (1987), J. Mol. Biol., 196:901-917; Chothia et al., (1989), Nature, 342:877-883; Caton et al., (1990), J. Immunol., 144:1965-1968; Sharon et al., (1990a), PNAS, 87:4814-4817; Sharon et al., (1990b), J. Immunol., 144: 4863-4869; Kabat et al., (1991b), J. Immunol., 147:1709-1719).

An antigen binding site forming part of an antibody molecule for use in the invention preferably has the CDRs of antibody F8 set forth in SEQ ID NOs 6-11, the CDRs of antibody L19 set forth in SEQ ID NOs 21-26, or the CDRs of antibody F16 set forth in SEQ ID NOs 30-35. Most preferably, an antigen binding site forming part of an antibody molecule for use in the invention has the CDRs of antibody F8 set forth in SEQ ID NOs 6-11.

Preparation and Selection of Antibody Molecules

Various methods are available in the art for obtaining antibodies molecules against a target antigen. The antibody molecules for use in the present invention are preferably monoclonal antibodies, especially of human, murine, chimeric or humanized origin, which can be obtained according to the standard methods well known to the person skilled in the art. An antibody molecule for use in the present invention is most preferably a human antibody molecule.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody molecule to the constant regions, or constant regions plus framework regions, of a different immunoglobulin. See, for instance, EP-A-184187, GB 2188638A or EP-A-239400, and a large body of subsequent literature. A hybridoma or other cell producing an antibody may also be subject to genetic mutation or other changes, which may or may not alter the binding specificity of antibodies produced.

Techniques available in the art of antibody engineering have made it possible to isolate human and humanised antibodies. For example, human hybridomas can be made as described by Kontermann & Dubel (2001), S, *Antibody Engineering*, Springer-Verlag New York, LLC; ISBN: 3540413545. Phage display, another established technique for generating specific binding members has been described in detail in many publications such as WO92/01047 (discussed further below) and U.S. Pat. Nos. 5,969,108, 5,565, 332, 5,733,743, 5,858,657, 5,871,907, 5,872,215, 5,885,793, 5,962,255, 6,140,471, 6,172,197, 6,225,447, 6,291,650, 6,492,160, 6,521,404 and Kontermann & Dubel (2001), S, *Antibody Engineering*, Springer-Verlag New York, LLC; ISBN: 3540413545. Transgenic mice in which the mouse antibody genes are inactivated and functionally replaced with human antibody genes while leaving intact other components of the mouse immune system, can be used for isolating human antibodies (Mendez et al., (1997), Nature Genet, 15(2): 146-156).

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein, 1975, Nature, 256:495-497.

Monoclonal antibodies can be obtained, for example, from an animal cell immunized against the an antigen associated with neoplastic growth and/or angiogenesis, such as A-FN, B-FN, tenascin C, the ED-A of fibronectin, the ED-B of fibronectin, or the A1 Domain of Tenascin C, according to the usual working methods, by genetic recombination starting with a nucleic acid sequence contained in the cDNA sequence coding for A-FN, B-FN, or tenascin C, or fragment thereof, or by peptide synthesis starting from a sequence of amino acids comprised in the peptide sequence of the A-FN, B-FN, or tenascin C, and/or a fragment thereof.

Synthetic antibody molecules may be created by expression from genes generated by means of oligonucleotides synthesized and assembled within suitable expression vectors, for example as described by Knappik et al. (2000) J. Mol. Biol. 296, 57-86 or Krebs et al. (2001) Journal of Immunological Methods, 254 67-84.

Alternatively, one or more antibody molecules for an antigen associated with neoplastic growth and/or angiogenesis, such as the A-FN, the ED-A, B-FN, the ED-B, tenascin C, or the A1 domain of tenascin C may be obtained by bringing into contact a library of antibody molecules and the antigen or a fragment thereof, e.g. a fragment comprising or consisting of ED-A, ED-B, or the A1 domain of tenascin C, or a peptide fragment thereof, and selecting one or more antibody molecules of the library able to bind the antigen.

An antibody library may be screened using Iterative Colony Filter Screening (ICFS). In ICFS, bacteria containing the DNA encoding several binding specificities are grown in a liquid medium and, once the stage of exponential growth has been reached, some billions of them are distributed onto a growth support consisting of a suitably pretreated membrane filter which is incubated until completely confluent bacterial colonies appear. A second trap substrate consists of another membrane filter, pre-humidified and covered with the desired antigen.

The trap membrane filter is then placed onto a plate containing a suitable culture medium and covered with the growth filter with the surface covered with bacterial colonies pointing upwards. The sandwich thus obtained is incubated at room temperature for about 16 h. It is thus possible to obtain the expression of the genes encoding antibody fragments scFv having a spreading action, so that those fragments binding specifically with the antigen which is present on the trap membrane are trapped. The trap membrane is then treated to point out bound antibody fragments scFv with colorimetric techniques commonly used to this purpose.

The position of the coloured spots on the trap filter allows one to go back to the corresponding bacterial colonies which are present on the growth membrane and produced the antibody fragments trapped. Such colonies are gathered and grown and the bacteria-a few millions of them are distributed onto a new culture membrane repeating the procedures described above. Analogous cycles are then carried out until the positive signals on the trap membrane correspond to single positive colonies, each of which represents a potential source of monoclonal antibody fragments directed against the antigen used in the selection. ICFS is described in e.g. WO0246455.

A library may also be displayed on particles or molecular complexes, e.g. replicable genetic packages such bacteriophage (e.g. T7) particles, or other in vitro display systems, each particle or molecular complex containing nucleic acid encoding the antibody VH variable domain displayed on it, and optionally also a displayed VL domain if present. Phage display is described in WO92/01047 and e.g. U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404.

Following selection of antibody molecules able to bind the antigen and displayed on bacteriophage or other library particles or molecular complexes, nucleic acid may be taken from a bacteriophage or other particle or molecular complex displaying a said selected antibody molecule. Such nucleic acid may be used in subsequent production of an antibody molecule or an antibody VH or VL variable domain by expression from nucleic acid with the sequence of nucleic acid taken from a bacteriophage or other particle or molecular complex displaying a said selected antibody molecule.

Ability to bind an antigen associated with neoplastic growth and/or angiogenesis, such as the A-FN, B-FN, the ED-A, or the ED-B of fibronectin, tenascin C or the A1 domain of tenascin C or other target antigen or isoform may be further tested, e.g. ability to compete with an antibody specific for the A-FN, B-FN, the ED-A, or the ED-B of fibronectin, tenascin C or the A1 domain of tenascin C, such as antibody F8, L19, or F16.

Novel VH or VL regions carrying CDR-derived sequences for use in the invention may be also generated using random mutagenesis of one or more selected VH and/or VL genes to generate mutations within the entire variable domain. In some embodiments one or two amino acid substitutions are made within an entire variable domain or set of CDRs. Another method that may be used is to direct mutagenesis to CDR regions of VH or VL genes.

Variable domains employed in the invention may be obtained or derived from any germ-line or rearranged human variable domain, or may be a synthetic variable domain based on consensus or actual sequences of known human variable domains. A variable domain can be derived from a non-human antibody. A CDR sequence for use in the invention (e.g. CDR3) may be introduced into a repertoire of variable domains lacking a CDR (e.g. CDR3), using recombinant DNA technology. For example, Marks et al. (1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide antibody molecules for use in the invention. The repertoire may then be displayed in a suitable host system such as the phage display system of WO92/01047, or any of a subsequent large body of literature, including Kay, Winter & McCafferty (1996), so that suitable antibody molecules may be selected. A repertoire may consist of from anything from $10^4$ individual members upwards, for example at least $10^5$, at least $10^6$, at least $10^7$, at least $10^8$, at least $10^9$ or at least $10^{10}$ members.

An antigen associated with neoplastic growth and/or angiogenesis, such as the A-FN, B-FN, the ED-A, or the ED-B of fibronectin, tenascin C or the A1 domain of tenascin C may be used in a screen for antibody molecules, e.g. antibody molecules, for use in the invention. The screen may a screen of a repertoire as disclosed elsewhere herein.

Similarly, one or more, or all three CDRs may be grafted into a repertoire of VH or VL domains that are then screened for an antibody molecule or antibody molecules for an antigen associated with neoplastic growth and/or angiogenesis, such as A-FN, B-FN, the ED-A, or the ED-B of fibronectin, tenascin C or the A1 domain of tenascin C. One or more of the HCDR1, HCDR2 and HCDR3 of antibody F8, L19, or F16, or the set of HCDRs of antibody F8, L19, or F16 may be employed, and/or one or more of the LCDR1, LCDR2 and LCDR3 of antibody F8, L19, or F16 the set of LCDRs of antibody F8, L19, or F16 may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of antibody molecules of the present invention made by recombinant DNA techniques may result in the introduction of N- or C-terminal residues encoded by linkers introduced to facilitate cloning or other manipulation steps. Other manipulation steps include the introduction of linkers to join variable domains disclosed elsewhere herein to further protein sequences including antibody constant regions, other variable domains (for example in the production of diabodies) or detectable/functional labels as discussed in more detail elsewhere herein.

Although antibody molecules may comprise a pair of VH and VL domains, single binding domains based on either VH or VL domain sequences may also be used in the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain antibody molecule able to bind an antigen associated with neoplastic growth and/or angiogenesis, such as A-FN, B-FN, the ED-A, or the ED-B of fibronectin, tenascin C or the A1 domain of tenascin C. This may be achieved by phage display screening methods using the so-called hierarchical dual combinatorial approach as disclosed in WO92/01047, in which an individual colony containing either an H or L chain clone is used to infect a complete library of clones encoding the other chain (L or H) and the resulting two-chain antibody molecule is selected in accordance with phage display techniques such as those described in that reference. This technique is also disclosed in Marks 1992.

Fragments of whole antibodies for use in the invention can be obtained starting from any of the antibody molecules described herein, e.g. antibody molecules comprising VH and/or VL domains or CDRs of any of antibodies described herein, by methods such as digestion by enzymes, such as pepsin or papain and/or by cleavage of the disulfide bridges by chemical reduction. In another manner, antibody fragments may be obtained by techniques of genetic recombination likewise well known to the person skilled in the art or else by peptide synthesis by means of, for example, automatic peptide synthesizers such as those supplied by the company Applied Biosystems, etc., or by nucleic acid synthesis and expression.

Conjugate

A conjugate according to the present invention comprises IL2 and a tumour necrosis factor, preferably TNFα, and an antibody molecule which binds an antigen associated with neoplastic growth and/or angiogenesis, as described herein. The antibody molecule is preferably an scFv or a diabody, most preferably an scFv, as described herein.

The IL2 and the tumour necrosis factor, are preferably human IL2 and human TNF. Where the tumour necrosis factor is TNFα, the TNFα is preferably human TNFα.

The IL2 preferably comprises or consist of the sequence set forth in SEQ ID NO: 12. Typically, IL2 has at least 70%, more preferably one of at least 75%, 80%, 85%, 90%, 95%, 96%, 97%, 98%, 99% or 100%, sequence identity to the amino acid sequence set forth in SEQ ID NO: 12. IL2 in conjugates of the invention retains a biological activity of human IL2, e.g. the ability to inhibit cell proliferation.

Human TNFα consists of a 35 amino acid cytoplasmic domain, a 21 amino acid transmembrane domain and a 177 amino acid extracellular domain. The 177 amino acid extracellular domain is cleaved to produce a 157 amino acid soluble form, which is biologically active, and which forms a non-covalently linked trimer in solution. In the context of the present invention, the human TNFα is preferably the soluble form of the extracellular domain of human TNFα, or the extracellular domain of human TNFα. The sequence of the soluble form of the extracellular domain of human TNFα is shown in SEQ ID NO: 15. The TNFα thus preferably comprises or consist of the sequence set forth in SEQ ID NO: 15. Typically, TNFα has at least 70%, more preferably one of at least 75%, 80%, 85%, 90%, 95%, 96%, 97%, 98%, 99% or 100%, sequence identity to the amino acid sequence set forth in SEQ ID NO: 15. The sequence of the extracellular domain of human TNFα is shown in SEQ ID NO: 40. Thus, alternatively the TNFα may comprise or consist of the sequence set forth in SEQ ID NO: 40. In this case, the TNFα may have at least 70%, more preferably one of at least 75%, 80%, 85%, 90%, 95%, 96%, 97%, 98%, 99% or 100%, sequence identity to the amino acid sequence set forth in SEQ ID NO: 40. TNFα in conjugates of the invention retains a biological activity of human TNFα, e.g. the ability to inhibit cell proliferation. Most preferably, the IL2 has, or comprises, the sequence set forth in SEQ ID NO: 12 and/or the TNFα has, or comprises, the sequence set forth in SEQ ID NO: 15.

Preferably, the antibody molecule is connected to the IL2 and a tumour necrosis factor, preferably TNFα, through linkers, for example a peptide linkers. Similarly, the IL2 and the tumour necrosis factor may be connected through linkers, for example a peptide linkers. Alternatively, the antibody molecule and IL2 and/or a tumour necrosis factor, may be connected directly, e.g. through a chemical bond. Where the antibody molecule is linked to IL2 and a tumour necrosis factor by means of one or more peptide linkers, or the IL2 and the tumour necrosis factor are linked to each other and the antibody molecule by means of one or more peptide linkers, the conjugate may be a fusion protein. By "fusion protein" is meant a polypeptide that is a translation product resulting from the fusion of two or more genes or nucleic acid coding sequences into one open reading frame (ORF).

The chemical bond may be, for example, a covalent or ionic bond. Examples of covalent bonds include peptide bonds (amide bonds) and disulphide bonds. The antibody molecule and IL2 and/or a tumour necrosis factor, preferably TNFα, may be covalently linked, for example by peptide bonds (amide bonds). Thus, the antibody molecule, in particular an scFv portion of an antibody molecule, and IL2 and/or a tumour necrosis factor, preferably TNFα, may be produces as a fusion protein.

Where the antibody molecule is a two-chain or multi-chain molecule (e.g. a diabody), IL2 and/or a tumour necrosis factor, preferably TNFα, may be conjugated as a fusion protein with one or more polypeptide chains in the antibody molecule.

The peptide linker connecting the antibody molecule and IL2 and/or a tumour necrosis factor, preferably TNFα, may be a flexible peptide linker. Similarly, the linker connecting connecting IL2 and a tumour necrosis factor in some of the conjugates of the invention may be a flexible peptide linker. Suitable examples of peptide linker sequences are known in the art. The linker may be 10-20 amino acids, preferably 10-15 amino acids in length. Most preferably, the linker is 11-15 amino acids in length. The linker may have the sequence set forth in SEQ ID NO: 13 or SEQ ID NO: 14. Preferably, the IL2 and a tumour necrosis factor, preferably TNFα, are linked to the antibody molecule by the linkers set forth in SEQ ID NO: 13 and SEQ ID NO: 14, respectively. In an alternative preferred embodiment, the IL2 is linked to the VL domain of the antibody via the linker set forth in SEQ ID NO: 14 and the tumour necrosis factor, preferably TNFα, is linked to the IL2 by the linker set forth in SEQ ID NO: 13.

In the conjugate employed in Examples 1 to 6, IL2 was conjugated to the VH domain of the F8 scFv and the TNFα was conjugated to the VL domain of the F8 scFv, each via a peptide linker as shown in SEQ ID NO: 1. However, it is expected that the conjugate would show the same or similar tumour targeting properties, and/or therapeutic efficacy, if the tumour necrosis factor and IL2 were conjugated to the antibody molecule in a different format. For example, it is expected the conjugate would show the same or similar tumour targeting properties, and/or therapeutic efficacy, if the tumour necrosis factor, preferably TNFα, was conjugated to the VH domain and the IL2 was conjugated to the VL domain of the antibody molecule, such as an scFv or diabody, preferably via peptide linkers. This is demonstrated in Example 7 which shows that the cell killing activity of such a conjugate is not statistically significantly different from that of a conjugate in which the IL2 was conjugated to the VH domain of the F8 scFv and the TNFα was conjugated to the VL domain of the F8 scFv. Thus, where the antibody molecule is, or comprises, an scFv, the IL2 may be linked to the N-terminus of the VH domain of the scFv via a peptide linker and the TNFα may be linked to the C-terminus of the VL domain of the scFv via a peptide linker. Alternatively, where the antibody molecule is, or comprises, an scFv, the TNFα may be linked to the N-terminus of the VH domain of the scFv via a peptide linker and the IL2 may be linked to the C-terminus of the VL domain of the scFv via a peptide linker. Example 7 further demonstrates that the cell killing activity of a conjugate in which both IL2 and TNFα were conjugated to the VL domain of the F8 scFv is not statistically significantly different from that of a conjugate in which the IL2 was conjugated to the VH domain of the F8 scFv and the TNFα was conjugated to the VL domain of the F8 scFv. It is expected, based on these results, that a conjugate would have the same or similar tumour targeting properties, and/or therapeutic efficacy, and/or cell killing activity if both IL2 and a tumour necrosis factor, preferably TNFα, were conjugated to the VH domain of the antibody. As a further alternative the IL2 and tumour necrosis factor, preferably TNFα, may therefore be linked to the C-terminus of the VL domain of the antibody, e.g. in scFv format, via a peptide linker. As a yet further alternative the IL2 and tumour necrosis factor, preferably TNFα, may be linked to the N-terminus of the VH domain of the antibody, e.g. in scFv format, via a peptide linker. In the latter two conjugates, the IL2 and TNFα may be in any order and/or may optionally be linked to one another via a peptide linker. Suitable peptide linkers are described herein.

The conjugate of the present invention may comprise or consist of the sequence shown in SEQ ID NO: 1. In this embodiment, the conjugate may have at least 70%, more preferably one of at least 75%, 80%, 85%, 90%, 95%, 96%, 97%, 98%, 99% or 100%, sequence identity to the amino acid sequence shown in SEQ ID NO: 1.

Alternatively, the conjugate of the present invention may comprise or consist of the sequence shown in SEQ ID NO: 39. In this embodiment, the conjugate may have at least 70%, more preferably one of at least 75%, 80%, 85%, 90%, 95%, 96%, 97%, 98%, 99% or 100%, sequence identity to the amino acid sequence shown in SEQ ID NO: 39.

The conjugate of the present invention may comprise or consist of the sequence shown in SEQ ID NO: 41. In this embodiment, the conjugate may have at least 70%, more preferably one of at least 75%, 80%, 85%, 90%, 95%, 96%, 97%, 98%, 99% or 100%, sequence identity to the amino acid sequence shown in SEQ ID NO: 41.

The conjugate of the present invention may comprise or consist of the sequence shown in SEQ ID NO: 42. In this embodiment, the conjugate may have at least 70%, more preferably one of at least 75%, 80%, 85%, 90%, 95%, 96%, 97%, 98%, 99% or 100%, sequence identity to the amino acid sequence shown in SEQ ID NO: 42.

The conjugate of the present invention may comprise or consist of the sequence shown in SEQ ID NO: 43. In this embodiment, the conjugate may have at least 70%, more preferably one of at least 75%, 80%, 85%, 90%, 95%, 96%, 97%, 98%, 99% or 100%, sequence identity to the amino acid sequence shown in SEQ ID NO: 43.

The conjugate of the present invention may comprise or consist of the sequence shown in SEQ ID NO: 44. In this embodiment, the conjugate may have at least 70%, more preferably one of at least 75%, 80%, 85%, 90%, 95%, 96%, 97%, 98%, 99% or 100%, sequence identity to the amino acid sequence shown in SEQ ID NO: 44.

Without being limited by any theoretical explanation, it is expected that a conjugate according to the present invention comprising TNFα will form a homotrimer in solution as soluble TNFα is known to homotrimerise. Such a trimeric conjugate would comprise three molecules of active IL2 to one molecule of active TNF (in trimeric structure). This may be advantageous as IL2-based immunocytokines are typically used in the clinic at higher doses compared to TNFα-based immunocytokines. For example, the recommended dose of L19-IL2 was found to be 4 mg in patients with cancer [Johannsen et al. (2010) Eur. J. Cancer], while the recommended dose of L19-TNFα is in the 1-1.5 mg dose range [Spitaleri et al. (2012) *J. Clin. Oncol. Cancer Res.*]. Thus, the conjugates of the invention may have advantageous properties with respect to administration regimens.

Nucleic Acids

Also provided is an isolated nucleic acid molecule encoding a conjugate according to the present invention. Nucleic acid molecules may comprise DNA and/or RNA and may be partially or wholly synthetic. Reference to a nucleotide sequence as set out herein encompasses a DNA molecule with the specified sequence, and encompasses a RNA molecule with the specified sequence in which U is substituted for T, unless context requires otherwise.

Further provided are constructs in the form of plasmids, vectors (e.g. expression vecotors), transcription or expression cassettes which comprise such nucleic acids. Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate. For further details see, for example, Sambrook & Russell (2001) Molecular Cloning: a Laboratory Manual: 3rd edition, Cold Spring Harbor Laboratory Press. Many known techniques and protocols for manipulation of nucleic acid, for example in the preparation of nucleic acid constructs, mutagenesis, sequencing, introduction of DNA into cells and gene expression, and analysis of proteins, are described in detail in Ausubel et al. (1999) $4^{th}$ eds., Short Protocols in Molecular Biology: A Compendium of Methods from Current Protocols in Molecular Biology, John Wiley & Sons.

Host Cells

A recombinant host cell that comprises one or more constructs as described above is also provided. Suitable host cells include bacteria, mammalian cells, plant cells, filamentous fungi, yeast and baculovirus systems and transgenic plants and animals.

A conjugate according to the present invention may be produced using such a recombinant host cell. The production method may comprise expressing a nucleic acid or construct as described above. Expression may conveniently be achieved by culturing the recombinant host cell under appropriate conditions for production of the conjugate. Following production the conjugate may be isolated and/or purified using any suitable technique, and then used as appropriate. The conjugate may be formulated into a composition including at least one additional component, such as a pharmaceutically acceptable excipient.

Systems for cloning and expression of a polypeptide in a variety of different host cells are well known. The expression of antibodies, including conjugates thereof, in prokaryotic cells is well established in the art. For a review, see for example Plückthun (1991), Bio/Technology 9: 545-551. A common bacterial host is *E.coli*.

Expression in eukaryotic cells in culture is also available to those skilled in the art as an option for production of conjugates for example Chadd et al. (2001), Current Opinion in Biotechnology 12: 188-194); Andersen et al. (2002) Current Opinion in Biotechnology 13: 117; Larrick & Thomas (2001) Current Opinion in Biotechnology 12:411-418. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

A method comprising introducing a nucleic acid or construct disclosed herein into a host cell is also described. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The nucleic acid may or construct be integrated into the genome (e.g. chromosome) of the host cell. Integration may be promoted by inclusion of sequences that promote recombination with the genome, in accordance with standard techniques.

Isolated

This refers to the state in which conjugates of the invention, antibodies for use in the invention, or nucleic acid encoding such conjugates, will generally be in accordance with the present invention. Thus, conjugates of the present invention, antibodies for use in the invention, or nucleic acid encoding such conjugates may be provided in isolated and/or purified, e.g. from the environment in which they are prepared (such as cell culture), in substantially pure or homogeneous form, or, in the case of nucleic acid, free or substantially free of nucleic acid other than the sequence encoding a polypeptide with the required function. Isolated members and isolated nucleic acids will be free or substantially free of material with which they are found in the environment in which they are prepared (e.g. cell culture) when such preparation is by recombinant DNA technology practised in vitro or in vivo. Specific conjugates and nucleic acids may be formulated with diluents or adjuvants and still for practical purposes be isolated—for example the members may be mixed with pharmaceutically acceptable carriers or diluents when used in therapy. Specific conjugates may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations of conjugates may also be used in the invention. For example, such preparations may be mixtures of conjugates comprising antibody molecules with full-length heavy chains and heavy chains lacking the C-terminal lysine, with various degrees of glycosylation and/or with derivatized amino acids, such as cyclization of an N-terminal glutamic acid to form a pyroglutamic acid residue.

Fibronectin

Fibronectin is an antigen subject to alternative splicing, and a number of alternative isoforms of fibronectin are known, including alternatively spliced isoforms A-FN and B-FN, comprising domains ED-A or ED-B respectively, which are known markers of angiogenesis. An antibody molecule, as referred to herein, may selectively bind to isoforms of fibronectin selectively expressed in the neovasculature. An antibody molecule may bind fibronectin isoform A-FN, e.g. it may bind domain ED-A (extra domain A). An antibody molecule may bind ED-B (extra domain B).

Fibronectin Extra Domain-A (EDA or ED-A) is also known as ED, extra type III repeat A (EIIIA) or EDI. The sequence of human ED-A has been published by Kornblihtt et al. (1984), Nucleic Acids Res. 12, 5853-5868 and Paolella et al. (1988), Nucleic Acids Res. 16, 3545-3557. The sequence of human ED-A is also available on the SwissProt database as amino acids 1631-1720 (Fibronectin type-III 12; extra domain 2) of the amino acid sequence deposited under accession number P02751. The sequence of mouse ED-A is available on the SwissProt database as amino acids 1721-1810 (Fibronectin type-III 13; extra domain 2) of the amino acid sequence deposited under accession number P11276.

The ED-A isoform of fibronectin (A-FN) contains the Extra Domain-A (ED-A). The sequence of the human A-FN can be deduced from the corresponding human fibronectin precursor sequence which is available on the SwissProt database under accession number P02751. The sequence of the mouse A-FN can be deduced from the corresponding mouse fibronectin precursor sequence which is available on the SwissProt database under accession number P11276. The A-FN may be the human ED-A isoform of fibronectin. The ED-A may be the Extra Domain-A of human fibronectin.

ED-A is a 90 amino acid sequence which is inserted into fibronectin (FN) by alternative splicing and is located between domain 11 and 12 of FN (Borsi et al. (1987), *J. Cell. Biol.*, 104, 595-600). ED-A is mainly absent in the plasma form of FN but is abundant during embryogenesis, tissue remodelling, fibrosis, cardiac transplantation and solid tumour growth.

Fibronectin isoform B-FN is one of the best known markers angiogenesis (U.S. Pat. No. 10/382,107, WO01/62298). An extra domain "ED-B" of 91 amino acids is found in the B-FN isoform and is identical in mouse, rat, rabbit, dog and man. B-FN accumulates around neovascular structures in aggressive tumours and other tissues undergoing angiogenesis, such as the endometrium in the proliferative phase and some ocular structures in pathological conditions, but is otherwise undetectable in normal adult tissues.

Tenascin C

Tenascin-C is a large hexameric glycoprotein of the extracellular matrix which modulates cellular adhesion. It is involved in processes such as cell proliferation and cell migration and is associated with changes in tissue architecture as occurring during morphogenesis and embryogenesis as well as under tumourigenesis or angiogenesis. Several isoforms of tenascin-C can be generated as a result of alternative splicing which may lead to the inclusion of (multiple) domains in the central part of this protein, ranging from domain A1 to domain D (Borsi L et al Int J Cancer 1992; 52:688-692, Carnemolla B et al. Eur J Biochem 1992; 205:561-567, WO2006/050834). An antibody molecule, as referred to herein, may bind tenascin-C. An antibody molecule may bind tenascin-C domain A1.

Cancer

Cancer, as referred to herein, may be a cancer which expresses, or has been shown to express, an antigen associated with neoplastic growth and/or angiogenesis, such as an extracellular matrix component associated with neoplastic growth and/or angiogenesis. Preferably, the cancer is a cancer which expresses, or has been shown to express, the ED-A isoform of fibronectin, the ED-B isoform of fibronectin and/or alternatively spliced tenascin C. More preferably the cancer expresses the ED-A isoform of fibronectin. For example, the cancer may be any type of solid or non-solid cancer or malignant lymphoma. The cancer may be selected from the group consisting of skin cancer (in particular melanoma), head and neck cancer, kidney cancer, sarcoma, germ cell cancer (such as teratocarcinoma), liver cancer, lymphoma (such as Hodgkin's or non-Hodgkin's lymphoma), leukaemia (e.g. acute myeloid leukaemia), skin cancer, bladder cancer, breast cancer, uterine cancer, ovarian cancer, prostate cancer, lung cancer, colorectal cancer, cervical cancer, oesophageal cancer, pancreatic cancer, stomach cancer, and cerebral cancer. Cancers may be familial or sporadic. Cancers may be metastatic or non-metastatic. Preferably, the cancer is a cancer selected from the group consisting of a melanoma, head and neck cancer, kidney cancer, and a sarcoma. The reference to a cancer as mentioned above normally refers to a malignant transformation of the cells in question. Thus, kidney cancer, for example, refers to a malignant transformation of cells in the kidney. The cancer may be located at its primary location, such as the kidney in the case of kidney cancer, or at a distant location in the case of metastases. A tumour as referred to herein may be the result of any of the cancers mentioned above. Preferably, a tumour is the result of a melanoma, head and neck cancer, kidney cancer, or a sarcoma. A tumour which is the result of a particular cancer includes both a primary tumour and tumour metastases of said cancer. Thus, a tumour which is the result of head and neck cancer, for example, includes both a primary tumour of head and neck and cancer and metastases of head and neck cancer found in other parts of a patient's body.

Treatment

It is expected that the conjugates of the invention will have anti-tumour activity and thus find application in cancer treatment. Without being limited by any theoretical explanation, it is expected that the conjugates of the invention will show potent anti-tumour activity as a result of excellent tumour targeting properties, as demonstrated in Example 5 below. The conjugates of the present invention are thus designed to be used in methods of treatment of patients, preferably human patients. Conjugates of the present invention may in particular be used in the treatment of cancer.

Accordingly, the invention provides methods of treatment comprising administration of a conjugate according to the present invention, pharmaceutical compositions comprising such conjugates, and use of such a conjugates in the manufacture of a medicament for administration, for example in a method of making a medicament or pharmaceutical composition comprising formulating the conjugate with a pharmaceutically acceptable excipient. Pharmaceutically acceptable vehicles are well known and will be adapted by the person skilled in the art as a function of the nature and of the mode of administration of the active compound(s) chosen.

Conjugates according to the present invention will usually be administered in the form of a pharmaceutical composition, which may comprise at least one component in addition to the antibody molecule. Thus, pharmaceutical compositions described herein, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be by injection, e.g. intravenous or subcutaneous. Preferably, the conjugate of the present invention is administered intravenously.

Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required. Many methods for the preparation of pharmaceutical formulations are known to those skilled in the art. See e.g. Robinson ed., Sustained and Controlled Release Drug Delivery Systems, Marcel Dekker, Inc., New York, 1978.

A composition comprising a conjugate according to the present invention may be administered alone or in combination with other cancer treatments, concurrently or sequentially or as a combined preparation with another therapeutic agent or agents, for the treatment of cancer. For example, a conjugate of the invention may be used in combination with an existing therapeutic agent for cancer.

A conjugate according to the invention may be used in the manufacture of a medicament. The medicament may be for separate or combined administration to an individual, and accordingly may comprise the conjugate and the additional component as a combined preparation or as separate preparations. Separate preparations may be used to facilitate separate and sequential or simultaneous administration, and allow administration of the components by different routes.

In accordance with the present invention, compositions provided may be administered to mammals, preferably humans. Administration may be in a "therapeutically effective amount", this being sufficient to show benefit to a patient. Such benefit may be at least amelioration of at least one symptom. Thus "treatment" of a specified disease refers to amelioration of at least one symptom. The actual amount administered, and rate and time-course of administration, will depend on the nature and severity of what is being treated, the particular patient being treated, the clinical condition of the individual patient, the cause of the disorder, the site of delivery of the composition, the type of conjugate, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of antibody are well known in the art (Ledermann et al. (1991) Int. J. Cancer 47: 659-664; and Bagshawe et al. (1991) Antibody, Immunoconjugates and Radiopharmaceuticals 4: 915-922). Specific dosages indicated herein, or in the Physician's Desk Reference (2003) as appropriate for the type of medicament being administered, may be used. A therapeutically effective amount or suitable dose of a conjugate for use in the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the conjugate. A typical conjugate dose will be in the range 100 µg to 1 g for systemic applications. An initial higher loading dose, followed by one or more lower doses, may be administered. This is a dose for a single treatment of an adult patient, which may be proportionally adjusted for children and infants, and also adjusted according to conjugate format in proportion to molecular weight. Treatments may be repeated at daily, twice-weekly, weekly or monthly intervals, at the discretion of the physician. Treatments may be every two to four weeks for subcutaneous administration and every four to eight weeks for intravenous administration. In some embodiments of the present invention, treatment is periodic, and the period between administrations is about two weeks or more, e.g. about three weeks or more, about four weeks or more, or about once a month. In other embodiments of the invention, treatment may be given before, and/or after surgery, and may be administered or applied directly at the anatomical site of surgical treatment.

EXAMPLES

Example 1

Size Exclusion Chromatography

The purified muIL2-F8-muTNFα conjugate (SEQ ID NO: 16) was analysed on an ÄKTA-FPLC system with a Superdex 200 HR 10/30 column. Gel filtration analysis revealed two peaks as shown in FIG. 1. The peak with retention volume 11.5 mL corresponded to a trimeric fraction of the conjugate, which was collected for further experiments (i.e. biodistribution; see below). The trimeric fraction comprised trimers of the muIL2-F8-muTNFα conjugate, formed by association of three TNFα molecules to form a trimeric protein. The peak at a retention volume of 9.9 mL represents a non-covalent-multimeric species of the conjugate.

Example 2

SDS-PAGE Analysis

Figure 2:
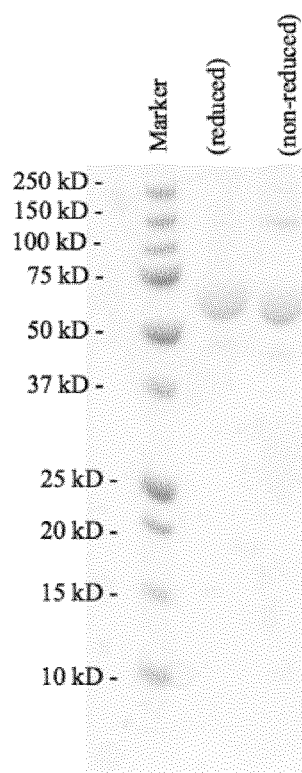
FIG. 2 shows the results of SDS-PAGE analysis of the muIL2-F8-muTNFα conjugate. The band at 62 kDa corresponds to the expected molecular weight of the muIL2-F8-muTNFα conjugate.

The purified muIL2-F8-muTNFα conjugate was characterized by SDS-PAGE analysis under non-reducing and reducing conditions, confirming the presence of a single band of apparent molecular weight equal to 62 kDa as shown in FIG. 2. This molecular weight corresponds to the expected molecular weight of the muIL2-F8-muTNFα conjugate.

Example 3

ELISA

Figure 3:
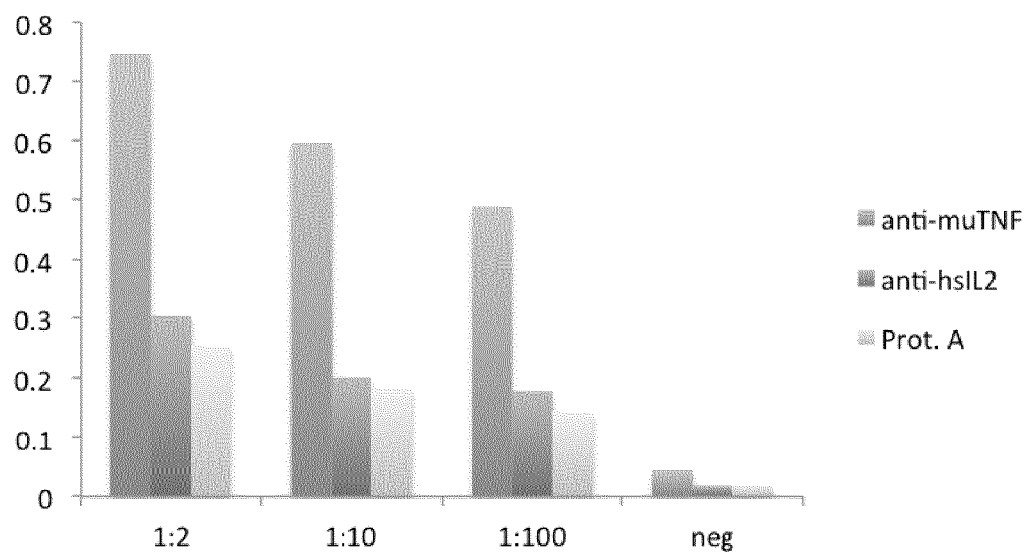
FIG. 3 shows the results of an ELISA performed on the muIL2-F8-muTNFα conjugate. A polypeptide containing ED-A was coated on the wells and detected by the muIL2-F8-muTNFα conjugate followed by detection of the constituents of the conjugate using detection antibodies. All three constituents of the conjugate, i.e. IL2, TNFα and the scFv F8 could be detected at the different dilutions tested and were therefore present in the conjugate. The y-axis shows the $OD_{450}$.

Biotinylated 11-EDA-12 domain of fibronectin, which includes the epitope recognized by scFv(F8), was immobilized on a streptavidin-coated plate (StreptaWell, Roche Applied Bioscience). Three different detection systems were used and allowed the evaluation of the expression of the different components of the muIL2-F8-muTNFα conjugate. Horseradish peroxidase-conjugated protein A (GE Healthcare) was used to detect the VH domain of the ScFv(F8). In order to detect IL2, a rat monoclonal antibody against hu-IL2 (eBioscience) was used, while to detect TNFα a rat monoclonal antibody against mu-TNFα (eBioscience) was used; both of these antibodies were detected with a goat anti-rat IgG peroxidase conjugate (Sigma-Aldrich). The enzyme reaction was detected using the BluePOD substrate (Roche Diagnostics) followed by measuring the photometric absorbance at 450 nm. FIG. 3 shows that all constituents of the muIL2-F8-muTNFα conjugate (i.e. IL2, TNFα and the scFv F8) could be detected at all three dilutions tested and were therefore present in the conjugate as expected. The dilution factors are shown below the x-axis in FIG. 3.

Example 4

BIAcore analysis

Figure 4:
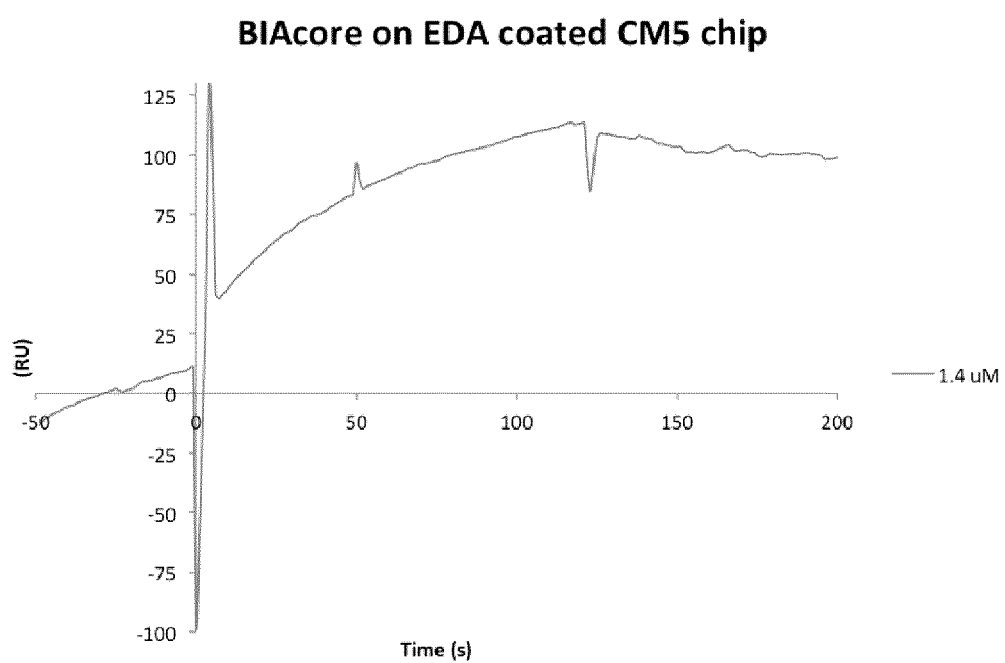
FIG. 4 shows the results of a BIAcore analysis to determine binding of the muIL2-F8-muTNFα conjugate to the Extra-Domain A (EDA) of fibronectin. The results demonstrate that the conjugate retains the ability to bind to EDA, the cognate antigen of the scFv F8 antibody.

The binding affinity of the muIL2-F8-muTNFα conjugate was measured through surface plasmon resonance analysis (BIAcore® 3000 system, GE healthcare) using a CM5 microsensor chip coated with 11-EDA-12. The muIL2-F8-muTNFα was filtered through 0.22 µm filters and 30 µL injected were injected into the system with a flow rate of 10 µL/min. The results shown in FIG. 4 demonstrate that conjugate retains the ability to bind to the Extra-Domain A (EDA) of fibronectin, the cognate antigen of the scFv F8 antibody.

Example 5

Biodistribution Analysis

Figure 5:
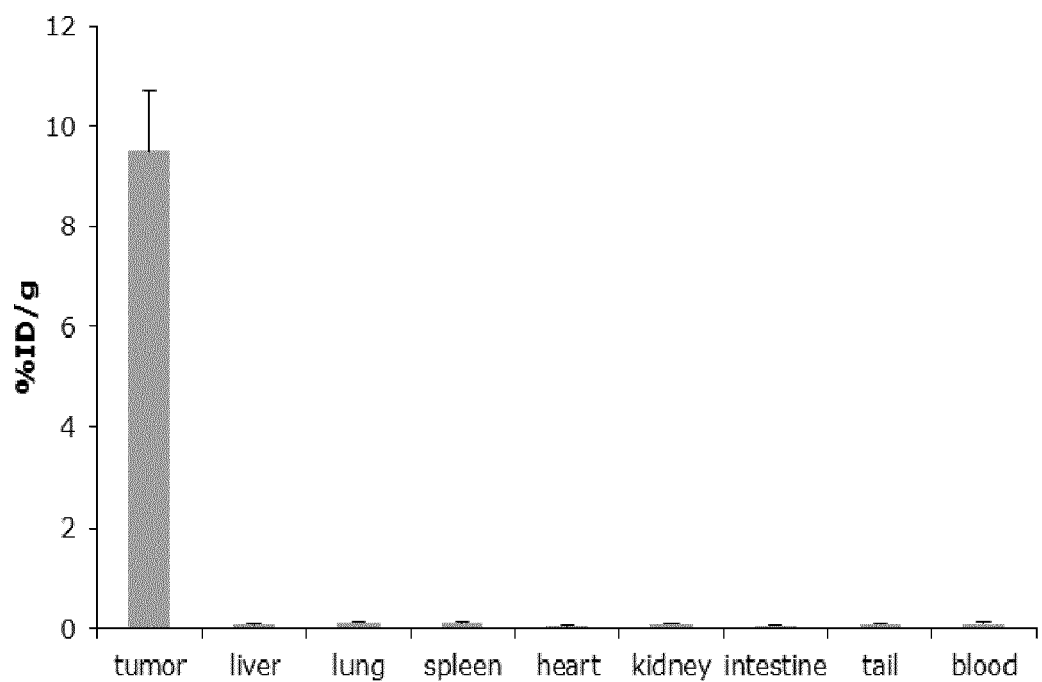
FIG. 5 shows the results of a biodistribution analysis of the muIL2-F8-muTNFα conjugate. The muIL2-F8-muTNFα conjugate selectively accumulated in tumours in a mouse model of F9 teratocarcinoma.

The in vivo targeting performance of the muIL2-F8-muTNFα conjugate was evaluated by biodistribution analysis. The homotrimeric fraction of muIL2-F8-muTNFα was purified on size exclusion chromatography as described in Example 1 above and then radioiodinated. 5 µg/2 µCi of conjugate labelled with $I^{125}$ were injected into the tail vein of immunocompetent 129SvEv mice bearing subcutaneous (s.c.) implanted F9 murine teratocarcinomas. Mice were sacrificed 24 h after injection. Organs were weighed and radioactivity was counted with a Packard Cobra gamma counter. The radioactive content of representative organs was expressed as the percentage of the injected dose per gram of tissue (% ID/g). FIG. 5 shows that the muIL2-F8-muTNFα conjugate selectively accumulated in the tumors, with average percent injected dose per gram (% ID/g) values of 9.5, representing an incorporation rate of 38%. The tumour targeting results obtained with the muIL2-F8-muTNFα conjugate were better than those previously reported for conjugates F8-IL2 and F8-TNFα (Hemmerle et al., 2013, Journal of Biotechnology, 172, 73-76; Pasche and Neri, 2012, Drug Discovery Today, doi:10.1016/j.drudis.2012.01.007). Specifically, Hemmerle et al. (2013) show in FIG. 2 that conjugate F8-TNFα achieved a % ID/g of about 3.5 in the same mouse model of F9 murine teratocarcinomas. Similarly, Pasche and Neri (2012) report in FIG. 2 that tumour targeting of conjugates F8-IL2 when tested in a different cancer model was not very good, as indicated by "+". Indeed, the tumor to organ ratios observed 24 hours after intravenous administration with the muIL2-F8-muTNFα conjugate were among the best every reported for any antibody-based therapeutic agent.

Example 6

Therapeutic Activity

The therapeutic efficacy of the muIL2-F8-muTNFα conjugate in tumor-bearing mice was compared with the therapeutic efficacy observed with combined administration of the F8-muTNFα and F8-muIL2 conjugates.

Eight week old Balb/C mice were injected subcutaneously with 5×10⁶ Wehi-164 murine sarcoma cells. Mice were monitored daily and tumor volume was measured with a caliper (volume=length×width²×0.5). Treatment was started when tumors reached a volume of 80 mm³. The body weight of the mice was recorded daily and body weight change is shown in FIG. 6B as mean (±SEM), n=5 mice per group.

Figure 6:
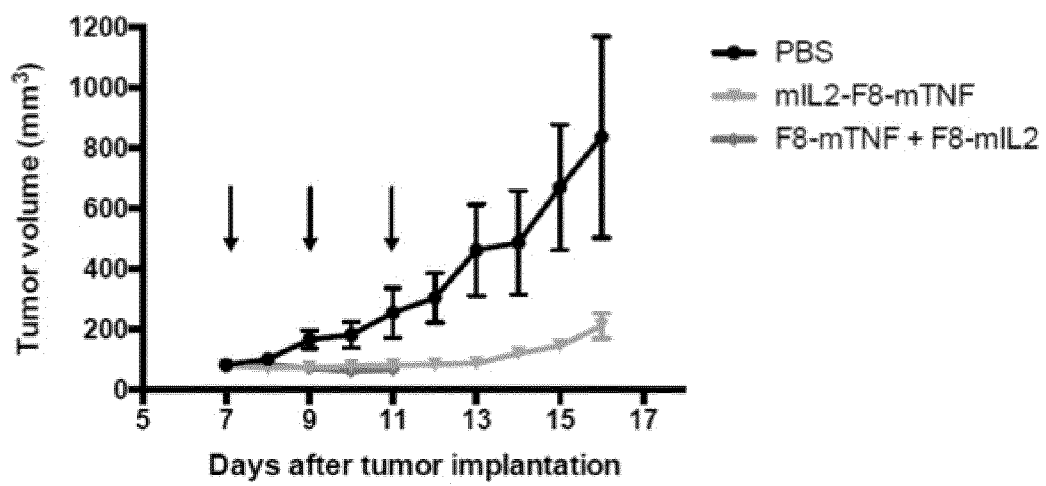
FIG. 6 shows the results of an experiment comparing the therapeutic efficacy of the muIL2-F8-muTNFα conjugate with combined administration of F8-muIL2 and F8-muTNFα. PBS was used as a negative control. The muIL2-F8-muTNFα conjugate retained the therapeutic efficacy seen with combinded administration of the single agents (FIG. 6A), whilst having remarkably lower toxicity (FIG. 6B).
Figure 6:
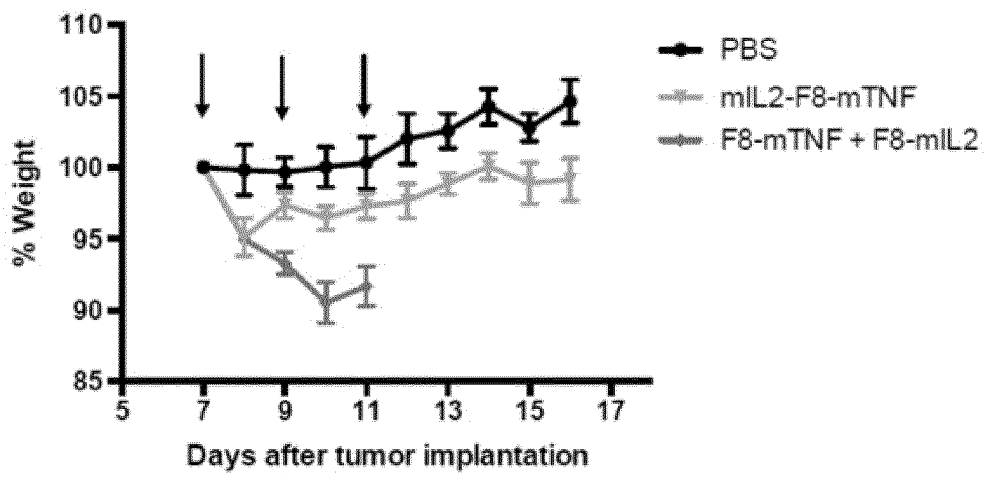

Mice were injected i.v. three times, 48 h apart (see black arrows in FIG. 6) with either PBS (negative control), 5.6 µg muIL2-F8-muTNFα or 4 µg F8-muTNFα in combination with 4 µg F8-muIL2. The amounts of the conjugates administered were selected to ensure that each mouse received equimolar amounts of IL2 and TNFα. The data shown in FIG. 6A represent the mean tumor volumes (±SEM), n=5 mice per group.

The antitumor activity, i.e. treatment efficacy, observed for muIL2-F8-muTNFα treatment was comparable to the antitumor activity observed with combined administration of F8-muTNFα and F8-muIL2 (see FIG. 6A).

In addition, the toxicity profile observed with muIL2-F8-muTNFα treatment was far superior to that observed with combined administration of F8-muTNFα and F8-muIL2 (see FIG. 6B), as evidenced by the reduced weight loss observed. Mice treated with the combination of conjugates had to be sacrificed after eleven days of treatment as a result of severe weight loss, while those treated with muIL2-F8-muTNFα treatment maintained acceptable weight until the end of the study at day 16. This demonstrates that treatment with muIL2-F8-muTNFα treatment is better tolerated than treatment with F8-muTNFα and F8-muIL2.

Example 7

Effect of Conjugate Format on Cell Killing Activity

Figure 7:
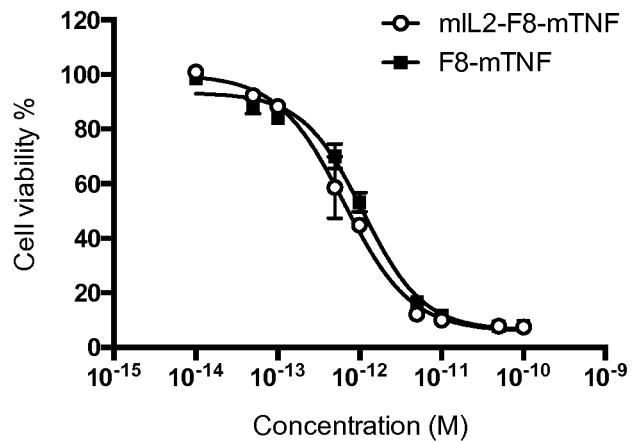
FIG. 7 shows the cell killing activity of three conjugates comprising TNFα, IL2 and the anti-ED-A antibody F8, with different formats. The conjugate formats tested were mIL2-F8-mTNFα (FIG. 7A), mTNFα-F8-mIL2 (FIG. 7B) and F8-mIL2-mTNFα (FIG. 7C). The cell killing activity of each conjugate was compared with the cell killing activity observed in the presence of conjugate F8-mTNFα as indicated below each figure.
Figure 7:
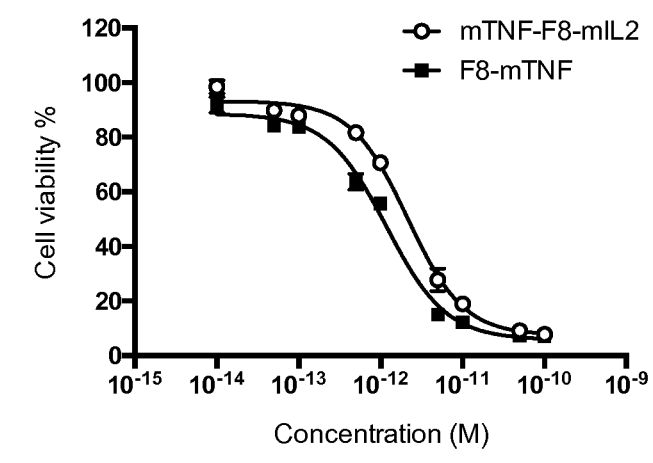
Figure 7:
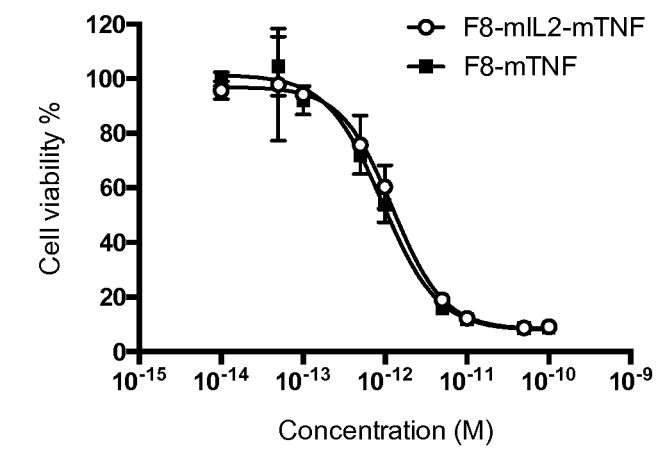

To test the significance of conjugate format on cell killing activity, the activity of different fusion protein formats was tested in a cell killing assay employing the mouse sarcoma WEHI-164 cell line. The assay was performed in the presence of 2 µg/mL actinomycin D (Sigma-Aldrich). Cells (30'000 cells/well) were seeded in 96-well plates in the culture medium supplemented with increasing concentrations of F8-mTNFα (SEQ ID NO: 47), mIL2-F8-mTNFα (SEQ ID NO: 17), mTNFα-F8-mIL2 (SEQ ID NO: 45) or F8-mIL2-mTNFα (SEQ ID NO: 46) as indicated in FIG. 7. The F8 antibody was in scFv format in all of the conjugates tested. After 24 h at 37° C., cell viability was determined using Cell Titer Aqueous One Solution (Promega). The results are shown in FIG. 7. Results are expressed as the percentage of cell viability compared to cells treated with actinomycin D only (used as the negative control). The results demonstrate that the cell killing activity of the different conjugate formats tested was comparable, as can be seen from the EC50 values reported in FIG. 7. The EC50 value represents the drug concentration required for half-maximal activity. There was no statistically significant difference between the EC50 values of the different conjugate formats. The R squared value for each EC50 value is also reported in FIG. 7. The closer R squared is to 1, the higher the reliability of the data. The data in FIG. 7 show a sigmoidal dose-response pattern (variable slope) and the regression line was fit using PRISM statistical software.

```
Sequence listing

Amino acid sequence of the huIL2-F8-huTNFα [soluble form] conjugate (SEQ ID NO: 1)
The amino acid sequence of the huIL2-F8-huTNFα [soluble form] conjugate (human IL2-
linker-F8 VH-linker-F8 VL-linker-human TNFα [soluble form]) is shown below. The linker
sequences are underlined. The human TNFα in this conjugate is the soluble form of the
extracellular domain of TNFα.
APTSSSTKKTQLQLEHLLLDLQMILNGINNYKNPKLTRMLTFKFYMPKKATELKHLQCLEEELKPLEEVLNL
AQSKNFHLRPRDLISNINVIVLELKGSETTFMCEYADETATIVEFLNRWITFCQSIISTLTGDGSSGGSGGA
SEVQLLESGGGLVQPGGSLRLSCAASGFTFSLFTMSWVRQAPGKGLEWVSAISGSGGSTYYADSVKGR
FTISRDNSKNTLYLQMNSLRAEDTAVYYCAKSTHLYLFDYWGQGTLVTVSSGGGGSGGGGSGGGGEIVL
TQSPGTLSLSPGERATLSCRASQSVSMPFLAWYQQKPGQAPRLLIYGASSRATGIPDRFSGSGSGTDFT
LTISRLEPEDFAVYYCQQMRGRPPTFGQGTKVEIKSSSSGSSSSGSSSSGVRSSSRTPSDKPVAHVVAN
PQAEGQLQWLNRRANALLANGVELRDNQLVVPSEGLYLIYSQVLFKGQGCPSTHVLLTHTISRIAVSYQT
KVNLLSAIKSPCQRETPEGAEAKPWYEPIYLGGVFQLEKGDRLSAEINRPDYLDFAESGQVYFGIIAL Amino acid sequence of the F8 VH domain (SEQ ID NO: 2)
EVQLLESGGGLVQPGGSLRLSCAASGFTFSLFTMSWVRQAPGKGLEWVSAISGSGGSTYYADSVKGRF
TISRDNSKNTLYLQMNSLRAEDTAVYYCAKSTHLYLFDYWGQGTLVTVSS Amino acid sequence of the linker linking the F8 VH domain to the F8 VL domain
(SEQ ID NO: 3)
GGGGSGGGGSGGGG Amino acid sequence of the F8 VL domain (SEQ ID NO: 4)
EIVLTQSPGTLSLSPGERATLSCRASQSVSMPFLAWYQQKPGQAPRLLIYGASSRATGIPDRFSGSGSGT
DFTLTISRLEPEDFAVYYCQQMRGRPPTFGQGTKVEIK Amino acid sequence of the F8 scFv (SEQ ID NO: 5)
EVQLLESGGGLVQPGGSLRLSCAASGFTFSLFTMSWVRQAPGKGLEWVSAISGSGGSTYYADSVKGRF
TISRDNSKNTLYLQMNSLRAEDTAVYYCAKSTHLYLFDYWGQGTLVTVSSGGGGSGGGGSGGGGEIVLT
```

```
QSPGTLSLSPGERATLSCRASQSVSMPFLAWYQQKPGQAPRLLIYGASSRATGIPDRFSGSGSGTDFTL
TISRLEPEDFAVYYCQQMRGRPPTFGQGTKVEIK

Amino acid sequences of the F8 CDR's
F8 CDR1 VH-LFT (SEQ ID NO: 6)

F8 CDR2 VH-SGSGGS (SEQ ID NO: 7)

F8 CDR3 VH-STHLYL (SEQ ID NO: 8)

F8 CDR1 VL-MPF (SEQ ID NO: 9)

F8 CDR2 VL-GASSRAT (SEQ ID NO: 10)

F8 CDR3 VL-MRGRPP (SEQ ID NO: 11)

Amino acid sequence of human IL2 (huIL2) in the huIL2-F8-huTNFα conjugates
(SEQ ID NO: 12)
APTSSSTKKTQLQLEHLLLDLQMILNGINNYKNPKLTRMLTFKFYMPKKATELKHLQCLEEELKPLEEVLNL
AQSKNFHLRPRDLISNINVIVLELKGSETTFMCEYADETATIVEFLNRWITFCQSIISTLT Amino acid sequence of the linker linking: huIL2 to the F8 VH domain in the huIL2-F8-
huTNFα conjugates, huTNFα to the F8 VH domain in the huTNFα-F8-huIL2 conjugates, and
huTNFα to huIL2 in the F8-huIL2-huTNFα conjugates (SEQ ID NO: 13)
GDGSSGGSGGAS Amino acid sequence of the linker linking: huTNFα to the F8 VL domain in the huIL2-
F8-huTNFα conjugates, huIL2 to the F8 VL domain in the huTNFα-F8-huIL2 conjugates,
and huIL2 to the F8 VL domain in the F8-huIL2-huTNFα conjugates (SEQ ID NO: 14)
SSSSGSSSSGSSSSG Amino acid sequence of the soluble form of the extracellular domain of human TNFα
(huTNFα) (SEQ ID NO: 15)
VRSSSRTPSDKPVAHVVANPQAEGQLQWLNRRANALLANGVELRDNQLVVPSEGLYLIYSQVLFKGQGC
PSTHVLLTHTISRIAVSYQTKVNLLSAIKSPCQRETPEGAEAKPWYEPIYLGGVFQLEKGDRLSAEINRPDY
LDFAESGQVYFGIIAL Amino acid sequence of the muIL2-F8-muTNFα conjugate (SEQ ID NO: 16)
The amino acid sequence of the muIL2-F8-muTNFα conjugate (murine IL2-linker-F8 VH-
linker-F8VL-linker-murine TNFα) is shown below. The linker sequences are underlined.
APTSSSTSSSTAEAQQQQQQQQQQQQHLEQLLMDLQELLSRMENYRNLKLPRMLTFKFYLPKQATELK
DLQCLEDELGPLRHVLDLTQSKSFQLEDAENFISNIRVTVVKLKGSDNTFECQFDDESATVVDFLRRWIAF
CQSIISTSPQGDGSSGGSGGASEVQLLESGGGLVQPGGSLRLSCAASGFTFSLFTMSWVRQAPGKGLE
WVSAISGSGGSTYYADSVKGRFTISRDNSKNTLYLQMNSLRAEDTAVYYCAKSTHLYLFDYWGQGTLVT
VSSGGGGSGGGGSGGGGEIVLTQSPGTLSLSPGERATLSCRASQSVSMPFLAWYQQKPGQAPRLLIYG
ASSRATGIPDRFSGSGSGTDFTLTISRLEPEDFAVYYCQQMRGRPPTFGQGTKVEIKSSSSGSSSSGSSS
SGLRSSSQNSSDKPVAHVVANHQVEEQLEWLSQRANALLANGMDLKDNQLVVPADGLYLVYSQVLFKG
QGCPDYVLLTHTVSRFAISYQEKVNLLSAVKSPCPKDTPEGAELKPWYEPIYLGGVFQLEKGDQLSAEVN
LPKYLDFAESGQVYFGVIAL Amino acid sequence of murine IL2 (muIL2) in the muIL2-F8-muTNFα conjugate (SEQ ID
NO: 17)
APTSSSTSSSTAEAQQQQQQQQQQQQHLEQLLMDLQELLSRMENYRNLKLPRMLTFKFYLPKQATELK
DLQCLEDELGPLRHVLDLTQSKSFQLEDAENFISNIRVTVVKLKGSDNTFECQFDDESATVVDFLRRWIAF
CQSIISTSPQ Amino acid sequence of the linker linking muIL2 to F8 VH domain in the muIL2-F8-
muTNFα conjugate (SEQ ID NO: 18)
GDGSSGGSGGAS Amino acid sequence of the linker linking muTNFα to the F8 VL domain in the muIL2-
F8-muTNFα conjugate (SEQ ID NO: 19)
SSSSGSSSSGSSSSG Amino acid sequence of murine TNFα (muTNFα) in the muIL2-F8-muTNFα conjugate (SEQ
ID NO: 20)
LRSSSQNSSDKPVAHVVANHQVEEQLEWLSQRANALLANGMDLKDNQLVVPADGLYLVYSQVLFKGQG
CPDYVLLTHTVSRFAISYQEKVNLLSAVKSPCPKDTPEGAELKPWYEPIYLGGVFQLEKGDQLSAEVNLP
KYLDFAESGQVYFGVIAL Amino acid sequence of L19 CDR's
L19 CDR1 VH-Ser Phe Ser Met Ser (SEQ ID NO: 21)

L19 CDR2 VH-Ser Ile Ser Gly Ser Ser Gly Thr Thr Tyr Tyr Ala Asp Ser Val Lys (SEQ
ID NO: 22)

L19 CDR3 VH-Pro Phe Pro Tyr Phe Asp Tyr (SEQ ID NO: 23)
```

L19 CDR1 VL-Arg Ala Ser Gln Ser Val Ser Ser Ser Phe Leu Ala (SEQ ID NO: 24)

L19 CDR2 VL-Tyr Ala Ser Ser Arg Ala Thr (SEQ ID NO: 25)

L19 CDR3 VL-Gln Gln Thr Gly Arg Ile Pro Pro Thr (SEQ ID NO: 26)

Amino acid sequence of L19 VH domain (SEQ ID NO: 27)
Glu Val Gln Leu Leu Glu Ser Gly Gly Gly Leu Val Gln Pro Gly Gly
Ser Leu Arg Leu Ser Cys Ala Ala Ser Gly Phe Thr Phe Ser Ser Phe
Ser Met Ser Trp Val Arg Gln Ala Pro Gly Lys Gly Leu Glu Trp Val
Ser Ser Ile Ser Gly Ser Ser Gly Thr Thr Tyr Tyr Ala Asp Ser Val
Lys Gly Arg Phe Thr Ile Ser Arg Asp Asn Ser Lys Asn Thr Leu Tyr
Leu Gln Met Asn Ser Leu Arg Ala Glu Asp Thr Ala Val Tyr Tyr Cys
Ala Lys Pro Phe Pro Tyr Phe Asp Tyr Trp Gly Gln Gly Thr Leu Val
Thr Val Ser Ser Amino acid sequence of L19 VL domain (SEQ ID NO: 28)
Glu Ile Val Leu Thr Gln Ser Pro Gly Thr Leu Ser Leu Ser Pro Gly
Glu Arg Ala Thr Leu Ser Cys Arg Ala Ser Gln Ser Val Ser Ser Ser
Phe Leu Ala Trp Tyr Gln Gln Lys Pro Gly Gln Ala Pro Arg Leu Leu
Ile Tyr Tyr Ala Ser Ser Arg Ala Thr Gly Ile Pro Asp Arg Phe Ser
Gly Ser Gly Ser Gly Thr Asp Phe Thr Leu Thr Ile Ser Arg Leu Glu
Pro Glu Asp Phe Ala Val Tyr Tyr Cys Gln Gln Thr Gly Arg Ile Pro
Pro Thr Phe Gly Gln Gly Thr Lys Val Glu Ile Lys Amino acid sequence of scFv(L19) (SEQ ID NO: 29)
Glu Val Gln Leu Leu Glu Ser Gly Gly Gly Leu Val Gln Pro Gly Gly
Ser Leu Arg Leu Ser Cys Ala Ala Ser Gly Phe Thr Phe Ser Ser Phe
Ser Met Ser Trp Val Arg Gln Ala Pro Gly Lys Gly Leu Glu Trp Val
Ser Ser Ile Ser Gly Ser Ser Gly Thr Thr Tyr Tyr Ala Asp Ser Val
Lys Gly Arg Phe Thr Ile Ser Arg Asp Asn Ser Lys Asn Thr Leu Tyr
Leu Gln Met Asn Ser Leu Arg Ala Glu Asp Thr Ala Val Tyr Tyr Cys
Ala Lys Pro Phe Pro Tyr Phe Asp Tyr Trp Gly Gln Gly Thr Leu Val
Thr Val Ser Ser Gly Asp Gly Ser Ser Gly Gly Ser Gly Gly Ala Ser
Glu Ile Val Leu Thr Gln Ser Pro Gly Thr Leu Ser Leu Ser Pro Gly
Glu Arg Ala Thr Leu Ser Cys Arg Ala Ser Gln Ser Val Ser Ser Ser
Phe Leu Ala Trp Tyr Gln Gln Lys Pro Gly Gln Ala Pro Arg Leu Leu
Ile Tyr Tyr Ala Ser Ser Arg Ala Thr Gly Ile Pro Asp Arg Phe Ser
Gly Ser Gly Ser Gly Thr Asp Phe Thr Leu Thr Ile Ser Arg Leu Glu
Pro Glu Asp Phe Ala Val Tyr Tyr Cys Gln Gln Thr Gly Arg Ile Pro
Pro Thr Phe Gly Gln Gly Thr Lys Val Glu Ile Lys Amino acid sequence of F16 CDR's
F16 CDR1 VH-RYGMS (SEQ ID NO: 30)

F16 CDR2 VH-AISGSGGSTYYADSVKG (SEQ ID NO: 31)

F16 CDR3 VH-AHNAFDY (SEQ ID NO: 32)

F16 CDR1 VL-QGDSLRSYYAS (SEQ ID NO: 33)

F16 CDR2 VL-GKNNRPS (SEQ ID NO: 34)

F16 CDR3 VL-NSSVYTMPPVV (SEQ ID NO: 35)

Amino acid sequence F16 VH domain (SEQ ID NO: 36)
EVQLLESGGGLVQPGGSLRLSCAASGFTFSRYGMSWVRQAPGKGLEWVSAISGSGGSTYYADSVKGR
FTISRDNSKNTLYLQMNSLRAEDTAVYYCAKAHNAFDYWGQGTLVTVSR Amino acid sequence F16 VL domain (SEQ ID NO: 37)
SSELTQDPAVSVALGQTVRITCQGDSLRSYYASWYQQKPGQAPVLVIYGKNNRPSGIPDRFSGSSSGNT
ASLTITGAQAEDEADYYCNSSVYTMPPVVFGGGTKLTVLG Amino acid sequence of the scFv(F16) (SEQ ID NO: 38)
The VH and VL domain linker sequence is shown underlined
EVQLLESGGGLVQPGGSLRLSCAASGFTFSRYGMSWVRQAPGKGLEWVSAISGSGGSTYYADSVKGR
FTISRDNSKNTLYLQMNSLRAEDTAVYYCAKAHNAFDYWGQGTLVTVSR<u>GGGSGGGSGGSS</u>ELTQDPA
VSVALGQTVRITCQGDSLRSYYASWYQQKPGQAPVLVIYGKNNRPSGIPDRFSGSSSGNTASLTITGAQA
EDEADYYCNSSVYTMPPVVFGGGTKLTVLG

```
Amino acid sequence of the huIL2-F8-huTNFα [extracellular domain] conjugate (SEQ ID
NO: 39)
The amino acid sequence of the huIL2-F8-huTNFα [extracellular domain] conjugate
(human IL2-linker-F8 VH-linker-F8 VL-linker-human TNFα [extracellular domain]) is
shown below. The linker sequences are underlined. The human TNFα in this conjugate is
the extracellular domain of TNFα.
APTSSSTKKTQLQLEHLLLDLQMILNGINNYKNPKLTRMLTFKFYMPKKATELKHLQCLEEELKPLEEVLNL
AQSKNFHLRPRDLISNINVIVLELKGSETTFMCEYADETATIVEFLNRWITFCQSIISTLTGDGSSGGSGGA
SEVQLLESGGGLVQPGGSLRLSCAASGFTFSLFTMSWVRQAPGKGLEWVSAISGSGGSTYYADSVKGR
FTISRDNSKNTLYLQMNSLRAEDTAVYYCAKSTHLYLFDYWGQGTLVTVSSGGGGSGGGGSGGGGEIVL
TQSPGTLSLSPGERATLSCRASQSVSMPFLAWYQQKPGQAPRLLIYGASSRATGIPDRFSGSGSGTDFT
LTISRLEPEDFAVYYCQQMRGRPPTFGQGTKVEIKSSSSGSSSSGSSSSGPQREEFPRDLSLISPLAQA
VRSSSRTPSDKPVAHVVANPQAEGQLQWLNRRANALLANGVELRDNQLVVPSEGLYLIYSQVLFKGQGC
PSTHVLLTHTISRIAVSYQTKVNLLSAIKSPCQRETPEGAEAKPWYEPIYLGGVFQLEKGDRLSAEINRPDY
LDFAESGQVYFGIIAL Amino acid sequence of the extracellular domain of human TNFα (huTNFα) (SEQ ID NO: 40)
GPQREEFPRDLSLISPLAQAVRSSSRTPSDKPVAHVVANPQAEGQLQWLNRRANALLANGVELRDNQLV
VPSEGLYLIYSQVLFKGQGCPSTHVLLTHTISRIAVSYQTKVNLLSAIKSPCQRETPEGAEAKPWYEPIYLG
GVFQLEKGDRLSAEINRPDYLDFAESGQVYFGIIAL Amino acid sequence of the huTNFα [soluble form]-F8-huIL2 conjugate (SEQ ID NO: 41)
The amino acid sequence of the huTNFα [soluble form]-F8-huIL2 conjugate (human TNFα
[soluble form]-linker-F8 VH-linker-F8 VL-linker-human IL2) is shown below. The linker
sequences are underlined.
VRSSSRTPSDKPVAHVVANPQAEGQLQWLNRRANALLANGVELRDNQLVVPSEGLYLIYSQVLFKGQGC
PSTHVLLTHTISRIAVSYQTKVNLLSAIKSPCQRETPEGAEAKPWYEPIYLGGVFQLEKGDRLSAEINRPDY
LDFAESGQVYFGIIALGDSSGGSGGASEVQLLESGGGLVQPGGSLRLSCAASGFTFSLFTMSWVRQAP
GKGLEWVSAISGSGGSTYYADSVKGRFTISRDNSKNTLYLQMNSLRAEDTAVYYCAKSTHLYLFDYWGQ
GTLVTVSSGGGGSGGGGSGGGGEIVLTQSPGTLSLSPGERATLSCRASQSVSMPFLAWYQQKPGQAP
RLLIYGASSRATGIPDRFSGSGSGTDFTLTISRLEPEDFAVYYCQQMRGRPPTFGQGTKVEIKSSSSGSS
SSGSSSSGAPTSSSTKKTQLQLEHLLLDLQMILNGINNYKNPKLTRMLTFKFYMPKKATELKHLQCLEEEL
KPLEEVLNLAQSKNFHLRPRDLISNINVIVLELKGSETTFMCEYADETATIVEFLNRWITFCQSIISTLT Amino acid sequence of the huTNFα [extracellular domain]-F8-huIL2 conjugate (SEQ ID
NO: 42)
The amino acid sequence of the huTNFα [extracellular domain]-F8-huIL2 conjugate
(human TNFα [extracellular domain]-linker-F8 VH-linker-F8 VL-linker-human IL2) is
shown below. The linker sequences are underlined.
GPQREEFPRDLSLISPLAQAVRSSSRTPSDKPVAHVVANPQAEGQLQWLNRRANALLANGVELRDNQLV
VPSEGLYLIYSQVLFKGQGCPSTHVLLTHTISRIAVSYQTKVNLLSAIKSPCQRETPEGAEAKPWYEPIYLG
GVFQLEKGDRLSAEINRPDYLDFAESGQVYFGIIALGDSSGGSGGASEVQLLESGGGLVQPGGSLRLS
CAASGFTFSLFTMSWVRQAPGKGLEWVSAISGSGGSTYYADSVKGRFTISRDNSKNTLYLQMNSLRAED
TAVYYCAKSTHLYLFDYWGQGTLVTVSSGGGGSGGGGSGGGGEIVLTQSPGTLSLSPGERATLSCRAS
QSVSMPFLAWYQQKPGQAPRLLIYGASSRATGIPDRFSGSGSGTDFTLTISRLEPEDFAVYYCQQMRGR
PPTFGQGTKVEIKSSSSGSSSSGSSSSGAPTSSSTKKTQLQLEHLLLDLQMILNGINNYKNPKLTRMLTFK
FYMPKKATELKHLQCLEEELKPLEEVLNLAQSKNFHLRPRDLISNINVIVLELKGSETTFMCEYADETATIVE
FLNRWITFCQSIISTLT Amino acid sequence of the F8-huIL2-huTNFα [soluble form] conjugate (SEQ ID NO: 43)
The amino acid sequence of the F8-huIL2-huTNFα [soluble form] conjugate (F8 VH-
linker-F8 VL-linker-human IL2-linker-human TNFα [soluble form]) is shown below. The
linker sequences are underlined.
EVQLLESGGGLVQPGGSLRLSCAASGFTFSLFTMSWVRQAPGKGLEWVSAISGSGGSTYYADSVKGRF
TISRDNSKNTLYLQMNSLRAEDTAVYYCAKSTHLYLFDYWGQGTLVTVSSGGGGSGGGGSGGGGEIVLT
QSPGTLSLSPGERATLSCRASQSVSMPFLAWYQQKPGQAPRLLIYGASSRATGIPDRFSGSGSGTDFTL
TISRLEPEDFAVYYCQQMRGRPPTFGQGTKVEIKSSSSGSSSSGSSSSGAPTSSSTKKTQLQLEHLLLDL
QMILNGINNYKNPKLTRMLTFKFYMPKKATELKHLQCLEEELKPLEEVLNLAQSKNFHLRPRDLISNINVIVL
ELKGSETTFMCEYADETATIVEFLNRWITFCQSIISTLTGDGSSGGSGGASVRSSSRTPSDKPVAHVVANP
QAEGQLQWLNRRANALLANGVELRDNQLVVPSEGLYLIYSQVLFKGQGCPSTHVLLTHTISRIAVSYQTK
VNLLSAIKSPCQRETPEGAEAKPWYEPIYLGGVFQLEKGDRLSAEINRPDYLDFAESGQVYFGIIAL Amino acid sequence of the F8-huIL2-huTNFα [extracellular domain] conjugate (SEQ ID
NO: 44)
The amino acid sequence of the F8-huIL2-huTNFα [extracellular domain] conjugate (F8
VH-linker-F8 VL-linker-human IL2-linker-human TNFα [extracellular domain]) is shown
below. The linker sequences are underlined.
EVQLLESGGGLVQPGGSLRLSCAASGFTFSLFTMSWVRQAPGKGLEWVSAISGSGGSTYYADSVKGRF
TISRDNSKNTLYLQMNSLRAEDTAVYYCAKSTHLYLFDYWGQGTLVTVSSGGGGSGGGGSGGGGEIVLT
QSPGTLSLSPGERATLSCRASQSVSMPFLAWYQQKPGQAPRLLIYGASSRATGIPDRFSGSGSGTDFT
TISRLEPEDFAVYYCQQMRGRPPTFGQGTKVEIKSSSSGSSSSGSSSSGAPTSSSTKKTQLQLEHLLLDL
QMILNGINNYKNPKLTRMLTFKFYMPKKATELKHLQCLEEELKPLEEVLNLAQSKNFHLRPRDLISNINVIVL
ELKGSETTFMCEYADETATIVEFLNRWITFCQSIISTLTGDGSSGGSGGASGPQREEFPRDLSLISPLAQA
VRSSSRTPSDKPVAHVVANPQAEGQLQWLNRRANALLANGVELRDNQLVVPSEGLYLIYSQVLFKGQGC
PSTHVLLTHTISRIAVSYQTKVNLLSAIKSPCQRETPEGAEAKPWYEPIYLGGVFQLEKGDRLSAEINRPDY
LDFAESGQVYFGIIAL
```

-continued

Sequence listing

Amino acid sequence of the muTNFα-F8-muIL2 conjugate (SEQ ID NO: 45)
The amino acid sequence of the muTNFα-F8-muIL2 conjugate (murine TNFα-linker-F8 VH-
linker-F8 VL-linker-murine IL2) is shown below. The linker sequences are underlined.
LRSSSQNSSDKPVAHVVANHQVEEQLEWLSQRANALLANGMDLKDNQLVVPADGLYLVYSQVLFKGQG
CPDYVLLTHTVSRFAISYQEKVNLLSAVKSPCPKDTPEGAELKPWYEPIYLGGVFQLEKGDQLSAEVNLP
KYLDFAESGQVYFGVIAL<u>GDSSGGSGGGAS</u>EVQLLESGGGLVQPGGSLRLSCAASGFTFSLFTMSWVR
QAPGKGLEWVSAISGSGGSTYYADSVKGRFTISRDNSKNTLYLQMNSLRAEDTAVYYCAKSTHLYLFDY
WGQGTLVTVSS<u>GGGGSGGGGSGGGGE</u>IVLTQSPGTLSLSPGERATLSCRASQSVSMPFLAWYQQKPG
QAPRLLIYGASSRATGIPDRFSGSGSGTDFTLTISRLEPEDFAVYYCQQMRGRPPTFGQGTKVEIK<u>SSSS
GSSSSGSSSSG</u>APTSSSTSSSTAEAQQQQQQQQQQQHLEQLLMDLQELLSRMENYRNLKLPRMLTF
KFYLPKQATELKDLQCLEDELGPLRHVLDLTQSKSFQLEDAENFISNIRVTVVKLKGSDNTFECQFDDESA
TVVDFLRRWIAFCQSIISTSPQ Amino acid sequence of the F8-muIL2-muTNFα conjugate (SEQ ID NO: 46)
The amino acid sequence of the F8-muIL2-muTNFα conjugate (F8 VH-linker-F8 VL-linker-
murine IL2-linker-murine TNFα) is shown below. The linker sequences are underlined.
EVQLLESGGGLVQPGGSLRLSCAASGFTFSLFTMSWVRQAPGKGLEWVSAISGSGGSTYYADSVKGRF
TISRDNSKNTLYLQMNSLRAEDTAVYYCAKSTHLYLFDYWGQGTLVTVSS<u>GGGGSGGGGSGGGGE</u>IVLT
QSPGTLSLSPGERATLSCRASQSVSMPFLAWYQQKPGQAPRLLIYGASSRATGIPDRFSGSGSGTDFTL
TISRLEPEDFAVYYCQQMRGRPPTFGQGTKVEIK<u>SSSSGSSSSGSSSSG</u>APTSSSTSSSTAEAQQQQQQ
QQQQQHLEQLLMDLQELLSRMENYRNLKLPRMLTFKFYLPKQATELKDLQCLEDELGPLRHVLDLTQS
KSFQLEDAENFISNIRVTVVKLKGSDNTFECQFDDESATVVDFLRRWIAFCQSIISTSPQ<u>GDGSSGGSGGA
SL</u>RSSSQNSSDKPVAHVVANHQVEEQLEWLSQRANALLANGMDLKDNQLVVPADGLYLVYSQVLFKGQ
GCPDYVLLTHTVSRFAISYQEKVNLLSAVKSPCPKDTPEGAELKPWYEPIYLGGVFQLEKGDQLSAEVNL
PKYLDFAESGQVYFGVIAL Amino acid sequence of F8-muTNFa conjugate (SEQ ID NO: 47)
EVQLLESGGGLVQPGGSLRLSCAASGFTFSLFTMSWVRQAPGKGLEWVSAISGSGGSTYYADSVKGRF
TISRDNSKNTLYLQMNSLRAEDTAVYYCAKSTHLYLFDYWGQGTLVTVSS<u>GGGGSGGGGSGGGGE</u>IVLT
QSPGTLSLSPGERATLSCRASQSVSMPFLAWYQQKPGQAPRLLIYGASSRATGIPDRFSGSGSGTDFTL
TISRLEPEDFAVYYCQQMRGRPPTFGQGTKVEIK<u>SSSSGSSSSGSSSSG</u>LRSSSQNSSDKPVAHVVANH
QVEEQLEWLSQRANALLANGMDLKDNQLVVPADGLYLVYSQVLFKGQGCPDYVLLTHTVSRFAISYQEK
VNLLSAVKSPCPKDTPEGAELKPWYEPIYLGGVFQLEKGDQLSAEVNLPKYLDFAESGQVYFGVIAL

SEQUENCE LISTING

<160> NUMBER OF SEQ ID NOS: 47

<210> SEQ ID NO 1
<211> LENGTH: 557
<212> TYPE: PRT
<213> ORGANISM: Artificial sequence
<220> FEATURE:
<223> OTHER INFORMATION: Synthetic Amino acid sequence of the
      huIL2-F8-huTNF alpha [soluble form] conjugate

<400> SEQUENCE: 1

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

```
Ile Ser Thr Leu Thr Gly Asp Gly Ser Ser Gly Ser Gly Gly Ala
130                 135                 140

Ser Glu Val Gln Leu Leu Glu Ser Gly Gly Leu Val Gln Pro Gly
145                 150                 155                 160

Gly Ser Leu Arg Leu Ser Cys Ala Ala Ser Gly Phe Thr Phe Ser Leu
                165                 170                 175

Phe Thr Met Ser Trp Val Arg Gln Ala Pro Gly Lys Gly Leu Glu Trp
                180                 185                 190

Val Ser Ala Ile Ser Gly Ser Gly Gly Ser Thr Tyr Tyr Ala Asp Ser
                195                 200                 205

Val Lys Gly Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Lys Ser Thr His Leu Tyr Leu Phe Asp Tyr Trp Gly Gln Gly
                245                 250                 255

Thr Leu Val Thr Val Ser Ser Gly Gly Gly Ser Gly Gly Gly
                260                 265                 270

Ser Gly Gly Gly Gly Glu Ile Val Leu Thr Gln Ser Pro Gly Thr Leu
    275                 280                 285

Ser Leu Ser Pro Gly Glu Arg Ala Thr Leu Ser Cys Arg Ala Ser Gln
290                 295                 300

Ser Val Ser Met Pro Phe Leu Ala Trp Tyr Gln Gln Lys Pro Gly Gln
305                 310                 315                 320

Ala Pro Arg Leu Leu Ile Tyr Gly Ala Ser Ser Arg Ala Thr Gly Ile
                325                 330                 335

Pro Asp Arg Phe Ser Gly Ser Gly Ser Gly Thr Asp Phe Thr Leu Thr
                340                 345                 350

Ile Ser Arg Leu Glu Pro Glu Asp Phe Ala Val Tyr Tyr Cys Gln Gln
                355                 360                 365

Met Arg Gly Arg Pro Pro Thr Phe Gly Gln Gly Thr Lys Val Glu Ile
                370                 375                 380

Lys Ser Ser Ser Ser Gly Ser Ser Ser Gly Ser Ser Ser Ser Gly
385                 390                 395                 400

Val Arg Ser Ser Arg Thr Pro Ser Asp Lys Pro Val Ala His Val
                405                 410                 415

Val Ala Asn Pro Gln Ala Glu Gly Gln Leu Gln Trp Leu Asn Arg Arg
                420                 425                 430

Ala Asn Ala Leu Leu Ala Asn Gly Val Glu Leu Arg Asp Asn Gln Leu
                435                 440                 445

Val Val Pro Ser Glu Gly Leu Tyr Leu Ile Tyr Ser Gln Val Leu Phe
450                 455                 460

Lys Gly Gln Gly Cys Pro Ser Thr His Val Leu Leu Thr His Thr Ile
465                 470                 475                 480

Ser Arg Ile Ala Val Ser Tyr Gln Thr Lys Val Asn Leu Leu Ser Ala
                485                 490                 495

Ile Lys Ser Pro Cys Gln Arg Glu Thr Pro Glu Gly Ala Glu Ala Lys
                500                 505                 510

Pro Trp Tyr Glu Pro Ile Tyr Leu Gly Gly Val Phe Gln Leu Glu Lys
                515                 520                 525

Gly Asp Arg Leu Ser Ala Glu Ile Asn Arg Pro Asp Tyr Leu Asp Phe
530                 535                 540

Ala Glu Ser Gly Gln Val Tyr Phe Gly Ile Ile Ala Leu
```

545          550          555

<210> SEQ ID NO 2
<211> LENGTH: 118
<212> TYPE: PRT
<213> ORGANISM: Artificial sequence
<220> FEATURE:
<223> OTHER INFORMATION: Synthetic Amino acid sequence of the F8 VH
      domain

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 3
<211> LENGTH: 14
<212> TYPE: PRT
<213> ORGANISM: Artificial sequence
<220> FEATURE:
<223> OTHER INFORMATION: Synthetic Amino acid sequence of the linker
      linking the F8 VH domain to the F8 VL domain

<400> SEQUENCE: 3

Gly Gly Gly Gly Ser Gly Gly Gly Gly Ser Gly Gly Gly Gly
1               5                   10

<210> SEQ ID NO 4
<211> LENGTH: 108
<212> TYPE: PRT
<213> ORGANISM: Artificial sequence
<220> FEATURE:
<223> OTHER INFORMATION: Synthetic Amino acid sequence of the F8 VL
      domain

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105

<210> SEQ ID NO 5
<211> LENGTH: 240
<212> TYPE: PRT
<213> ORGANISM: Artificial sequence
<220> FEATURE:
<223> OTHER INFORMATION: Synthetic Amino acid sequence of the F8 scFv

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Ser Met Pro Phe Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
            180                 185                 190

Asp Arg Phe Ser Gly Ser Gly Ser Gly Thr Asp Phe Thr Leu Thr Ile
        195                 200                 205

Ser Arg Leu Glu Pro Glu Asp Phe Ala Val Tyr Tyr Cys Gln Gln Met
    210                 215                 220

Arg Gly Arg Pro Pro Thr Phe Gly Gln Gly Thr Lys Val Glu Ile Lys
225                 230                 235                 240

<210> SEQ ID NO 6
<211> LENGTH: 3
<212> TYPE: PRT
<213> ORGANISM: Artificial sequence
<220> FEATURE:
<223> OTHER INFORMATION: Synthetic F8 CDR1 VH

<400> SEQUENCE: 6

Leu Phe Thr
1

<210> SEQ ID NO 7
<211> LENGTH: 6
<212> TYPE: PRT
<213> ORGANISM: Artificial sequence
<220> FEATURE:
<223> OTHER INFORMATION: Synthetic F8 CDR2 VH

```
<400> SEQUENCE: 7

Ser Gly Ser Gly Gly Ser
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic F8 CDR3 VH

<400> SEQUENCE: 8

Ser Thr His Leu Tyr Leu
1               5

<210> SEQ ID NO 9
<211> LENGTH: 3
<212> TYPE: PRT
<213> ORGANISM: Artificial sequence
<220> FEATURE:
<223> OTHER INFORMATION: Synthetic F8 CDR1 VL

<400> SEQUENCE: 9

Met Pro Phe
1

<210> SEQ ID NO 10
<211> LENGTH: 7
<212> TYPE: PRT
<213> ORGANISM: Artificial sequence
<220> FEATURE:
<223> OTHER INFORMATION: Synthetic F8 CDR2 VL

<400> SEQUENCE: 10

Gly Ala Ser Ser Arg Ala Thr
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic F8 CDR3 VL

<400> SEQUENCE: 11

Met Arg Gly Arg Pro Pro
1               5

<210> SEQ ID NO 12
<211> LENGTH: 133
<212> TYPE: PRT
<213> ORGANISM: Homo sapiens

<400> SEQUENCE: 12

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
```

```
                65                  70                  75                  80
Arg Pro Arg Asp Leu Ile Ser Asn Ile Asn Val Ile Val Leu Glu Leu
                        85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 13
<211> LENGTH: 12
<212> TYPE: PRT
<213> ORGANISM: Artificial sequence
<220> FEATURE:
<223> OTHER INFORMATION: Synthetic Amino acid sequence of the linker
      linking: huIL2 to the F8 VH domain in the huIL2-F8-huTNF alpha
      conjugates, huTNF alpha to the F8 VH domain in the huTNF
      alpha-F8-huIL2 conjugates, and huTNF alpha to huIL2 in the
      F8-huIL2-huTNF alpha conjugates

<400> SEQUENCE: 13

Gly Asp Gly Ser Ser Gly Gly Ser Gly Gly Ala Ser
1               5                   10

<210> SEQ ID NO 14
<211> LENGTH: 15
<212> TYPE: PRT
<213> ORGANISM: Artificial sequence
<220> FEATURE:
<223> OTHER INFORMATION: Synthetic Amino acid sequence of the linker
      linking: huTNF alpha to the F8 VL domain in the huIL2-F8-huTNF
      alpha conjugates, huIL2 to the F8 VL domain in the huTNF
      alpha-F8-huIL2 conjugates, and huIL2 to the F8 VL domain in the
      F8-huIL2-huTNF alpha conjugates

<400> SEQUENCE: 14

Ser Ser Ser Ser Gly Ser Ser Ser Gly Ser Ser Ser Gly
1               5                   10                  15

<210> SEQ ID NO 15
<211> LENGTH: 157
<212> TYPE: PRT
<213> ORGANISM: Homo sapiens

<400> SEQUENCE: 15

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125
```

-continued

```
Gly Asp Arg Leu Ser Ala Glu Ile Asn Arg Pro Asp Tyr Leu Asp Phe
            130                 135                 140

Ala Glu Ser Gly Gln Val Tyr Phe Gly Ile Ile Ala Leu
145                 150                 155

<210> SEQ ID NO 16
<211> LENGTH: 572
<212> TYPE: PRT
<213> ORGANISM: Artificial sequence
<220> FEATURE:
<223> OTHER INFORMATION: Synthetic Amino acid sequence of the
      muIL2-F8-muTNF alpha conjugate

<400> SEQUENCE: 16

Ala Pro Thr Ser Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
            35                  40                  45

Lys Leu Pro Arg Met Leu Thr Phe Lys Phe Tyr Leu Pro Lys Gln Ala
50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
            115                 120                 125

Val Val Asp Phe Leu Arg Arg Trp Ile Ala Phe Cys Gln Ser Ile Ile
130                 135                 140

Ser Thr Ser Pro Gln Gly Asp Gly Ser Ser Gly Gly Ser Gly Gly Ala
145                 150                 155                 160

Ser Glu Val Gln Leu Leu Glu Ser Gly Gly Gly Leu Val Gln Pro Gly
                165                 170                 175

Gly Ser Leu Arg Leu Ser Cys Ala Ala Ser Gly Phe Thr Phe Ser Leu
            180                 185                 190

Phe Thr Met Ser Trp Val Arg Gln Ala Pro Gly Lys Gly Leu Glu Trp
            195                 200                 205

Val Ser Ala Ile Ser Gly Ser Gly Gly Ser Thr Tyr Tyr Ala Asp Ser
            210                 215                 220

Val Lys Gly Arg Phe Thr Ile Ser Arg Asp Asn Ser Lys Asn Thr Leu
225                 230                 235                 240

Tyr Leu Gln Met Asn Ser Leu Arg Ala Glu Asp Thr Ala Val Tyr Tyr
                245                 250                 255

Cys Ala Lys Ser Thr His Leu Tyr Leu Phe Asp Tyr Trp Gly Gln Gly
            260                 265                 270

Thr Leu Val Thr Val Ser Ser Gly Gly Gly Gly Ser Gly Gly Gly Gly
            275                 280                 285

Ser Gly Gly Gly Gly Glu Ile Val Leu Thr Gln Ser Pro Gly Thr Leu
            290                 295                 300

Ser Leu Ser Pro Gly Glu Arg Ala Thr Leu Ser Cys Arg Ala Ser Gln
305                 310                 315                 320

Ser Val Ser Met Pro Phe Leu Ala Trp Tyr Gln Gln Lys Pro Gly Gln
```

```
            325                 330                 335
Ala Pro Arg Leu Leu Ile Tyr Gly Ala Ser Ser Arg Ala Thr Gly Ile
            340                 345                 350

Pro Asp Arg Phe Ser Gly Ser Gly Ser Gly Thr Asp Phe Thr Leu Thr
            355                 360                 365

Ile Ser Arg Leu Glu Pro Glu Asp Phe Ala Val Tyr Tyr Cys Gln Gln
            370                 375                 380

Met Arg Gly Arg Pro Pro Thr Phe Gly Gln Gly Thr Lys Val Glu Ile
385                 390                 395                 400

Lys Ser Ser Ser Gly Ser Ser Ser Gly Ser Ser Ser Gly
                    405                 410                 415

Leu Arg Ser Ser Ser Gln Asn Ser Ser Asp Lys Pro Val Ala His Val
            420                 425                 430

Val Ala Asn His Gln Val Glu Glu Gln Leu Glu Trp Leu Ser Gln Arg
            435                 440                 445

Ala Asn Ala Leu Leu Ala Asn Gly Met Asp Leu Lys Asp Asn Gln Leu
            450                 455                 460

Val Val Pro Ala Asp Gly Leu Tyr Leu Val Tyr Ser Gln Val Leu Phe
465                 470                 475                 480

Lys Gly Gln Gly Cys Pro Asp Tyr Val Leu Leu Thr His Thr Val Ser
                    485                 490                 495

Arg Phe Ala Ile Ser Tyr Gln Glu Lys Val Asn Leu Leu Ser Ala Val
            500                 505                 510

Lys Ser Pro Cys Pro Lys Asp Thr Pro Glu Gly Ala Glu Leu Lys Pro
            515                 520                 525

Trp Tyr Glu Pro Ile Tyr Leu Gly Gly Val Phe Gln Leu Glu Lys Gly
            530                 535                 540

Asp Gln Leu Ser Ala Glu Val Asn Leu Pro Lys Tyr Leu Asp Phe Ala
545                 550                 555                 560

Glu Ser Gly Gln Val Tyr Phe Gly Val Ile Ala Leu
                    565                 570

<210> SEQ ID NO 17
<211> LENGTH: 149
<212> TYPE: PRT
<213> ORGANISM: Mus musculus

<400> SEQUENCE: 17

Ala Pro Thr Ser Ser Ser Thr Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
            115                 120                 125
```

```
Val Val Asp Phe Leu Arg Arg Trp Ile Ala Phe Cys Gln Ser Ile Ile
        130                 135                 140

Ser Thr Ser Pro Gln
145

<210> SEQ ID NO 18
<211> LENGTH: 12
<212> TYPE: PRT
<213> ORGANISM: Artificial sequence
<220> FEATURE:
<223> OTHER INFORMATION: Synthetic Amino acid sequence of the linker
      linking muIL2 to F8 VH domain in the muIL2-F8-muTNF alpha
      conjugate

<400> SEQUENCE: 18

Gly Asp Gly Ser Ser Gly Gly Ser Gly Gly Ala Ser
1               5                   10

<210> SEQ ID NO 19
<211> LENGTH: 15
<212> TYPE: PRT
<213> ORGANISM: Artificial sequence
<220> FEATURE:
<223> OTHER INFORMATION: Synthetic Amino acid sequence of the linker
      linking muTNF alpha to the F8 VL domain in the muIL2-F8-muTNF
      alpha conjugate

<400> SEQUENCE: 19

Ser Ser Ser Ser Gly Ser Ser Ser Gly Ser Ser Ser Ser Gly
1               5                   10              15

<210> SEQ ID NO 20
<211> LENGTH: 156
<212> TYPE: PRT
<213> ORGANISM: Mus musculus

<400> SEQUENCE: 20

Leu Arg Ser Ser Ser Gln Asn Ser Ser Asp Lys Pro Val Ala His Val
1               5                   10                  15

Val Ala Asn His Gln Val Glu Glu Gln Leu Glu Trp Leu Ser Gln Arg
            20                  25                  30

Ala Asn Ala Leu Leu Ala Asn Gly Met Asp Leu Lys Asp Asn Gln Leu
        35                  40                  45

Val Val Pro Ala Asp Gly Leu Tyr Leu Val Tyr Ser Gln Val Leu Phe
    50                  55                  60

Lys Gly Gln Gly Cys Pro Asp Tyr Val Leu Leu Thr His Thr Val Ser
65                  70                  75                  80

Arg Phe Ala Ile Ser Tyr Gln Glu Lys Val Asn Leu Leu Ser Ala Val
                85                  90                  95

Lys Ser Pro Cys Pro Lys Asp Thr Pro Glu Gly Ala Glu Leu Lys Pro
            100                 105                 110

Trp Tyr Glu Pro Ile Tyr Leu Gly Gly Val Phe Gln Leu Glu Lys Gly
        115                 120                 125

Asp Gln Leu Ser Ala Glu Val Asn Leu Pro Lys Tyr Leu Asp Phe Ala
    130                 135                 140

Glu Ser Gly Gln Val Tyr Phe Gly Val Ile Ala Leu
145                 150                 155

<210> SEQ ID NO 21
<211> LENGTH: 5
<212> TYPE: PRT
<213> ORGANISM: Artificial sequence
```

```
<220> FEATURE:
<223> OTHER INFORMATION: Synthetic L19 CDR1 VH

<400> SEQUENCE: 21

Ser Phe Ser Met Ser
1               5

<210> SEQ ID NO 22
<211> LENGTH: 16
<212> TYPE: PRT
<213> ORGANISM: Artificial sequence
<220> FEATURE:
<223> OTHER INFORMATION: Synthetic L19 CDR2 VH

<400> SEQUENCE: 22

Ser Ile Ser Gly Ser Ser Gly Thr Thr Tyr Tyr Ala Asp Ser Val Lys
1               5                   10                  15

<210> SEQ ID NO 23
<211> LENGTH: 7
<212> TYPE: PRT
<213> ORGANISM: Artificial sequence
<220> FEATURE:
<223> OTHER INFORMATION: Synthetic L19 CDR3 VH

<400> SEQUENCE: 23

Pro Phe Pro Tyr Phe Asp Tyr
1               5

<210> SEQ ID NO 24
<211> LENGTH: 12
<212> TYPE: PRT
<213> ORGANISM: Artificial sequence
<220> FEATURE:
<223> OTHER INFORMATION: Synthetic L19 CDR1 VL

<400> SEQUENCE: 24

Arg Ala Ser Gln Ser Val Ser Ser Ser Phe Leu Ala
1               5                   10

<210> SEQ ID NO 25
<211> LENGTH: 7
<212> TYPE: PRT
<213> ORGANISM: Artificial sequence
<220> FEATURE:
<223> OTHER INFORMATION: Synthetic L19 CDR2 VL

<400> SEQUENCE: 25

Tyr Ala Ser Ser Arg Ala Thr
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic L19 CDR3 VL

<400> SEQUENCE: 26

Gln Gln Thr Gly Arg Ile Pro Pro Thr
1               5

<210> SEQ ID NO 27
<211> LENGTH: 116
<212> TYPE: PRT
<213> ORGANISM: Artificial sequence
<220> FEATURE:
```

<223> OTHER INFORMATION: Synthetic Amino acid sequence of L19 VH domain

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser
        115

<210> SEQ ID NO 28
<211> LENGTH: 108
<212> TYPE: PRT
<213> ORGANISM: Artificial sequence
<220> FEATURE:
<223> OTHER INFORMATION: Synthetic Amino acid sequence of L19 VL domain

<400> SEQUENCE: 28

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105

<210> SEQ ID NO 29
<211> LENGTH: 236
<212> TYPE: PRT
<213> ORGANISM: Artificial sequence
<220> FEATURE:
<223> OTHER INFORMATION: Synthetic Amino acid sequence of scFv(L19)

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Pro Phe Pro Tyr Phe Asp Tyr Trp Gly Gln Gly Thr Leu Val
                    100                 105                 110

Thr Val Ser Ser Gly Asp Gly Ser Gly Gly Ser Gly Gly Ala Ser
                115                 120                 125

Glu Ile Val Leu Thr Gln Ser Pro Gly Thr Leu Ser Leu Ser Pro Gly
            130                 135                 140

Glu Arg Ala Thr Leu Ser Cys Arg Ala Ser Gln Ser Val Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys
225                 230                 235

<210> SEQ ID NO 30
<211> LENGTH: 5
<212> TYPE: PRT
<213> ORGANISM: Artificial sequence
<220> FEATURE:
<223> OTHER INFORMATION: Synthetic F16 CDR1 VH

<400> SEQUENCE: 30

Arg Tyr Gly Met Ser
1               5

<210> SEQ ID NO 31
<211> LENGTH: 17
<212> TYPE: PRT
<213> ORGANISM: Artificial sequence
<220> FEATURE:
<223> OTHER INFORMATION: Synthetic F16 CDR2 VH

<400> SEQUENCE: 31

Ala Ile Ser Gly Ser Gly Gly Ser Thr Tyr Tyr Ala Asp Ser Val Lys
1               5                   10                  15

Gly

<210> SEQ ID NO 32
<211> LENGTH: 7
<212> TYPE: PRT
<213> ORGANISM: Artificial sequence
<220> FEATURE:
<223> OTHER INFORMATION: Synthetic F16 CDR3 VH

<400> SEQUENCE: 32

Ala His Asn Ala Phe Asp Tyr
1               5

<210> SEQ ID NO 33
<211> LENGTH: 11
```

```
<212> TYPE: PRT
<213> ORGANISM: Artificial sequence
<220> FEATURE:
<223> OTHER INFORMATION: Synthetic F16 CDR1 VL

<400> SEQUENCE: 33

Gln Gly Asp Ser Leu Arg Ser Tyr Tyr Ala Ser
1               5                   10

<210> SEQ ID NO 34
<211> LENGTH: 7
<212> TYPE: PRT
<213> ORGANISM: Artificial sequence
<220> FEATURE:
<223> OTHER INFORMATION: Synthetic F16 CDR2 VL

<400> SEQUENCE: 34

Gly Lys Asn Asn Arg Pro Ser
1               5

<210> SEQ ID NO 35
<211> LENGTH: 11
<212> TYPE: PRT
<213> ORGANISM: Artificial sequence
<220> FEATURE:
<223> OTHER INFORMATION: Synthetic F16 CDR3 VL

<400> SEQUENCE: 35

Asn Ser Ser Val Tyr Thr Met Pro Pro Val Val
1               5                   10

<210> SEQ ID NO 36
<211> LENGTH: 116
<212> TYPE: PRT
<213> ORGANISM: Artificial sequence
<220> FEATURE:
<223> OTHER INFORMATION: Synthetic Amino acid sequence F16 VH domain

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg
        115

<210> SEQ ID NO 37
<211> LENGTH: 109
<212> TYPE: PRT
<213> ORGANISM: Artificial sequence
<220> FEATURE:
<223> OTHER INFORMATION: Synthetic Amino acid sequence F16 VL domain

<400> SEQUENCE: 37
```

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Val Tyr Thr Met Pro Pro
                85                  90                  95

Val Val Phe Gly Gly Gly Thr Lys Leu Thr Val Leu Gly
            100                 105
```

<210> SEQ ID NO 38
<211> LENGTH: 235
<212> TYPE: PRT
<213> ORGANISM: Artificial sequence
<220> FEATURE:
<223> OTHER INFORMATION: Synthetic Amino acid sequence of the scFv(F16)

<400> SEQUENCE: 38

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg Gly Gly Gly Ser Gly Gly Gly Ser Gly Gly Ser Ser
            115                 120                 125

Glu Leu Thr Gln Asp Pro Ala Val Ser Val Ala Leu Gly Gln Thr Val
            130                 135                 140

Arg Ile Thr Cys Gln Gly Asp Ser Leu Arg Ser Tyr Tyr Ala Ser Trp
145                 150                 155                 160

Tyr Gln Gln Lys Pro Gly Gln Ala Pro Val Leu Val Ile Tyr Gly Lys
                165                 170                 175

Asn Asn Arg Pro Ser Gly Ile Pro Asp Arg Phe Ser Gly Ser Ser Ser
            180                 185                 190

Gly Asn Thr Ala Ser Leu Thr Ile Thr Gly Ala Gln Ala Glu Asp Glu
            195                 200                 205

Ala Asp Tyr Tyr Cys Asn Ser Val Tyr Thr Met Pro Pro Val Val
            210                 215                 220

Phe Gly Gly Gly Thr Lys Leu Thr Val Leu Gly
225                 230                 235
```

<210> SEQ ID NO 39

```
<211> LENGTH: 577
<212> TYPE: PRT
<213> ORGANISM: Artificial sequence
<220> FEATURE:
<223> OTHER INFORMATION: Synthetic Amino acid sequence of the
      huIL2-F8-huTNF alpha [extracellular domain] conjugate

<400> SEQUENCE: 39

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Asp Gly Ser Gly Ser Gly Gly Ala
130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Leu
                165                 170                 175

Phe Thr Met Ser Trp Val Arg Gln Ala Pro Gly Lys Gly Leu Glu Trp
            180                 185                 190

Val Ser Ala Ile Ser Gly Ser Gly Gly Ser Thr Tyr Tyr Ala Asp Ser
        195                 200                 205

Val Lys Gly Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Lys Ser Thr His Leu Tyr Leu Phe Asp Tyr Trp Gly Gln Gly
                245                 250                 255

Thr Leu Val Thr Val Ser Ser Gly Gly Gly Ser Gly Gly Gly Gly
            260                 265                 270

Ser Gly Gly Gly Gly Glu Ile Val Leu Thr Gln Ser Pro Gly Thr Leu
        275                 280                 285

Ser Leu Ser Pro Gly Glu Arg Ala Thr Leu Ser Cys Arg Ala Ser Gln
290                 295                 300

Ser Val Ser Met Pro Phe Leu Ala Trp Tyr Gln Gln Lys Pro Gly Gln
305                 310                 315                 320

Ala Pro Arg Leu Leu Ile Tyr Gly Ala Ser Ser Arg Ala Thr Gly Ile
                325                 330                 335

Pro Asp Arg Phe Ser Gly Ser Gly Ser Gly Thr Asp Phe Thr Leu Thr
            340                 345                 350

Ile Ser Arg Leu Glu Pro Glu Asp Phe Ala Val Tyr Tyr Cys Gln Gln
        355                 360                 365

Met Arg Gly Arg Pro Pro Thr Phe Gly Gln Gly Thr Lys Val Glu Ile
```

```
                370                 375                 380
Lys Ser Ser Ser Gly Ser Ser Ser Gly Ser Ser Ser Gly
385                 390                 395                 400

Gly Pro Gln Arg Glu Glu Phe Pro Arg Asp Leu Ser Leu Ile Ser Pro
                    405                 410                 415

Leu Ala Gln Ala Val Arg Ser Ser Arg Thr Pro Ser Asp Lys Pro
                420                 425                 430

Val Ala His Val Val Ala Asn Pro Gln Ala Glu Gly Gln Leu Gln Trp
            435                 440                 445

Leu Asn Arg Arg Ala Asn Ala Leu Leu Ala Asn Gly Val Glu Leu Arg
        450                 455                 460

Asp Asn Gln Leu Val Val Pro Ser Glu Gly Leu Tyr Leu Ile Tyr Ser
465                 470                 475                 480

Gln Val Leu Phe Lys Gly Gln Gly Cys Pro Ser Thr His Val Leu Leu
                    485                 490                 495

Thr His Thr Ile Ser Arg Ile Ala Val Ser Tyr Gln Thr Lys Val Asn
                500                 505                 510

Leu Leu Ser Ala Ile Lys Ser Pro Cys Gln Arg Glu Thr Pro Glu Gly
            515                 520                 525

Ala Glu Ala Lys Pro Trp Tyr Glu Pro Ile Tyr Leu Gly Gly Val Phe
        530                 535                 540

Gln Leu Glu Lys Gly Asp Arg Leu Ser Ala Glu Ile Asn Arg Pro Asp
545                 550                 555                 560

Tyr Leu Asp Phe Ala Glu Ser Gly Gln Val Tyr Phe Gly Ile Ile Ala
                    565                 570                 575

Leu

<210> SEQ ID NO 40
<211> LENGTH: 177
<212> TYPE: PRT
<213> ORGANISM: Homo sapiens

<400> SEQUENCE: 40

Gly Pro Gln Arg Glu Glu Phe Pro Arg Asp Leu Ser Leu Ile Ser Pro
1               5                   10                  15

Leu Ala Gln Ala Val Arg Ser Ser Arg Thr Pro Ser Asp Lys Pro
            20                  25                  30

Val Ala His Val Val Ala Asn Pro Gln Ala Glu Gly Gln Leu Gln Trp
        35                  40                  45

Leu Asn Arg Arg Ala Asn Ala Leu Leu Ala Asn Gly Val Glu Leu Arg
    50                  55                  60

Asp Asn Gln Leu Val Val Pro Ser Glu Gly Leu Tyr Leu Ile Tyr Ser
65                  70                  75                  80

Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
            100                 105                 110

Leu Leu Ser Ala Ile Lys Ser Pro Cys Gln Arg Glu Thr Pro Glu Gly
        115                 120                 125

Ala Glu Ala Lys Pro Trp Tyr Glu Pro Ile Tyr Leu Gly Gly Val Phe
    130                 135                 140

Gln Leu Glu Lys Gly Asp Arg Leu Ser Ala Glu Ile Asn Arg Pro Asp
145                 150                 155                 160

Tyr Leu Asp Phe Ala Glu Ser Gly Gln Val Tyr Phe Gly Ile Ile Ala
```

```
                    165                 170                 175
Leu

<210> SEQ ID NO 41
<211> LENGTH: 557
<212> TYPE: PRT
<213> ORGANISM: Artificial sequence
<220> FEATURE:
<223> OTHER INFORMATION: Synthetic Amino acid sequence of the huTNF
      alpha [soluble form]-F8-huIL2 conjugate

<400> SEQUENCE: 41

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu Gly Asp Gly
145                 150                 155                 160

Ser Ser Gly Gly Ser Gly Gly Ala Ser Glu Val Gln Leu Leu Glu Ser
                165                 170                 175

Gly Gly Gly Leu Val Gln Pro Gly Gly Ser Leu Arg Leu Ser Cys Ala
            180                 185                 190

Ala Ser Gly Phe Thr Phe Ser Leu Phe Thr Met Ser Trp Val Arg Gln
        195                 200                 205

Ala Pro Gly Lys Gly Leu Glu Trp Val Ser Ala Ile Ser Gly Ser Gly
    210                 215                 220

Gly Ser Thr Tyr Tyr Ala Asp Ser Val Lys Gly Arg Phe Thr Ile Ser
225                 230                 235                 240

Arg Asp Asn Ser Lys Asn Thr Leu Tyr Leu Gln Met Asn Ser Leu Arg
                245                 250                 255

Ala Glu Asp Thr Ala Val Tyr Tyr Cys Ala Lys Ser Thr His Leu Tyr
            260                 265                 270

Leu Phe Asp Tyr Trp Gly Gln Gly Thr Leu Val Thr Val Ser Ser Gly
        275                 280                 285

Gly Gly Gly Ser Gly Gly Gly Ser Gly Gly Gly Gly Glu Ile Val
    290                 295                 300

Leu Thr Gln Ser Pro Gly Thr Leu Ser Leu Ser Pro Gly Glu Arg Ala
305                 310                 315                 320

Thr Leu Ser Cys Arg Ala Ser Gln Ser Val Ser Met Pro Phe Leu Ala
                325                 330                 335

Trp Tyr Gln Gln Lys Pro Gly Gln Ala Pro Arg Leu Leu Ile Tyr Gly
```

```
            340                 345                 350
Ala Ser Ser Arg Ala Thr Gly Ile Pro Asp Arg Phe Ser Gly Ser Gly
        355                 360                 365

Ser Gly Thr Asp Phe Thr Leu Thr Ile Ser Arg Leu Glu Pro Glu Asp
    370                 375                 380

Phe Ala Val Tyr Tyr Cys Gln Gln Met Arg Gly Arg Pro Pro Thr Phe
385                 390                 395                 400

Gly Gln Gly Thr Lys Val Glu Ile Lys Ser Ser Ser Gly Ser Ser
                405                 410                 415

Ser Ser Gly Ser Ser Ser Gly Ala Pro Thr Ser Ser Ser Thr Lys
            420                 425                 430

Lys Thr Gln Leu Gln Leu Glu His Leu Leu Leu Asp Leu Gln Met Ile
        435                 440                 445

Leu Asn Gly Ile Asn Asn Tyr Lys Asn Pro Lys Leu Thr Arg Met Leu
    450                 455                 460

Thr Phe Lys Phe Tyr Met Pro Lys Lys Ala Thr Glu Leu Lys His Leu
465                 470                 475                 480

Gln Cys Leu Glu Glu Glu Leu Lys Pro Leu Glu Glu Val Leu Asn Leu
                485                 490                 495

Ala Gln Ser Lys Asn Phe His Leu Arg Pro Arg Asp Leu Ile Ser Asn
            500                 505                 510

Ile Asn Val Ile Val Leu Glu Leu Lys Gly Ser Glu Thr Thr Phe Met
        515                 520                 525

Cys Glu Tyr Ala Asp Glu Thr Ala Thr Ile Val Glu Phe Leu Asn Arg
    530                 535                 540

Trp Ile Thr Phe Cys Gln Ser Ile Ile Ser Thr Leu Thr
545                 550                 555

<210> SEQ ID NO 42
<211> LENGTH: 577
<212> TYPE: PRT
<213> ORGANISM: Artificial sequence
<220> FEATURE:
<223> OTHER INFORMATION: Synthetic Amino acid sequence of the huTNF
      alpha [extracellular domain]-F8-huIL2 conjugate

<400> SEQUENCE: 42

Gly Pro Gln Arg Glu Glu Phe Pro Arg Asp Leu Ser Leu Ile Ser Pro
1               5                   10                  15

Leu Ala Gln Ala Val Arg Ser Ser Arg Thr Pro Ser Asp Lys Pro
            20                  25                  30

Val Ala His Val Val Ala Asn Pro Gln Ala Glu Gly Gln Leu Gln Trp
        35                  40                  45

Leu Asn Arg Arg Ala Asn Ala Leu Leu Ala Asn Gly Val Glu Leu Arg
    50                  55                  60

Asp Asn Gln Leu Val Val Pro Ser Glu Gly Leu Tyr Leu Ile Tyr Ser
65                  70                  75                  80

Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
            100                 105                 110

Leu Leu Ser Ala Ile Lys Ser Pro Cys Gln Arg Glu Thr Pro Glu Gly
        115                 120                 125

Ala Glu Ala Lys Pro Trp Tyr Glu Pro Ile Tyr Leu Gly Gly Val Phe
    130                 135                 140
```

-continued

```
Gln Leu Glu Lys Gly Asp Arg Leu Ser Ala Glu Ile Asn Arg Pro Asp
145                 150                 155                 160

Tyr Leu Asp Phe Ala Glu Ser Gly Gln Val Tyr Phe Gly Ile Ile Ala
                165                 170                 175

Leu Gly Asp Gly Ser Ser Gly Gly Ser Gly Ala Ser Glu Val Gln
            180                 185                 190

Leu Leu Glu Ser Gly Gly Gly Leu Val Gln Pro Gly Gly Ser Leu Arg
        195                 200                 205

Leu Ser Cys Ala Ala Ser Gly Phe Thr Phe Ser Leu Phe Thr Met Ser
    210                 215                 220

Trp Val Arg Gln Ala Pro Gly Lys Gly Leu Glu Trp Val Ser Ala Ile
225                 230                 235                 240

Ser Gly Ser Gly Gly Ser Thr Tyr Tyr Ala Asp Ser Val Lys Gly Arg
                245                 250                 255

Phe Thr Ile Ser Arg Asp Asn Ser Lys Asn Thr Leu Tyr Leu Gln Met
                260                 265                 270

Asn Ser Leu Arg Ala Glu Asp Thr Ala Val Tyr Tyr Cys Ala Lys Ser
            275                 280                 285

Thr His Leu Tyr Leu Phe Asp Tyr Trp Gly Gln Gly Thr Leu Val Thr
        290                 295                 300

Val Ser Ser Gly Gly Gly Gly Ser Gly Gly Gly Ser Gly Gly Gly
305                 310                 315                 320

Gly Glu Ile Val Leu Thr Gln Ser Pro Gly Thr Leu Ser Leu Ser Pro
                325                 330                 335

Gly Glu Arg Ala Thr Leu Ser Cys Arg Ala Ser Gln Ser Val Ser Met
            340                 345                 350

Pro Phe Leu Ala Trp Tyr Gln Gln Lys Pro Gly Gln Ala Pro Arg Leu
        355                 360                 365

Leu Ile Tyr Gly Ala Ser Ser Arg Ala Thr Gly Ile Pro Asp Arg Phe
    370                 375                 380

Ser Gly Ser Gly Ser Gly Thr Asp Phe Thr Leu Thr Ile Ser Arg Leu
385                 390                 395                 400

Glu Pro Glu Asp Phe Ala Val Tyr Tyr Cys Gln Gln Met Arg Gly Arg
                405                 410                 415

Pro Pro Thr Phe Gly Gln Gly Thr Lys Val Glu Ile Lys Ser Ser Ser
            420                 425                 430

Ser Gly Ser Ser Ser Gly Ser Ser Ser Gly Ala Pro Thr Ser
        435                 440                 445

Ser Ser Thr Lys Lys Thr Gln Leu Gln Leu Glu His Leu Leu Leu Asp
    450                 455                 460

Leu Gln Met Ile Leu Asn Gly Ile Asn Asn Tyr Lys Asn Pro Lys Leu
465                 470                 475                 480

Thr Arg Met Leu Thr Phe Lys Phe Tyr Met Pro Lys Lys Ala Thr Glu
                485                 490                 495

Leu Lys His Leu Gln Cys Leu Glu Glu Glu Leu Lys Pro Leu Glu Glu
            500                 505                 510

Val Leu Asn Leu Ala Gln Ser Lys Asn Phe His Leu Arg Pro Arg Asp
        515                 520                 525

Leu Ile Ser Asn Ile Asn Val Ile Val Leu Glu Leu Lys Gly Ser Glu
    530                 535                 540

Thr Thr Phe Met Cys Glu Tyr Ala Asp Glu Thr Ala Thr Ile Val Glu
545                 550                 555                 560

Phe Leu Asn Arg Trp Ile Thr Phe Cys Gln Ser Ile Ile Ser Thr Leu
```

```
                    565                 570                 575

Thr

<210> SEQ ID NO 43
<211> LENGTH: 557
<212> TYPE: PRT
<213> ORGANISM: Artificial sequence
<220> FEATURE:
<223> OTHER INFORMATION: Synthetic Amino acid sequence of the
      F8-huIL2-huTNF alpha [soluble form] conjugate

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Gly Gly Gly Ser Gly Gly Gly Gly Ser
            115                 120                 125

Gly Gly Gly Gly Glu Ile Val Leu Thr Gln Ser Pro Gly Thr Leu Ser
130                 135                 140

Leu Ser Pro Gly Glu Arg Ala Thr Leu Ser Cys Arg Ala Ser Gln Ser
145                 150                 155                 160

Val Ser Met Pro Phe Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
            180                 185                 190

Asp Arg Phe Ser Gly Ser Gly Ser Gly Thr Asp Phe Thr Leu Thr Ile
        195                 200                 205

Ser Arg Leu Glu Pro Glu Asp Phe Ala Val Tyr Tyr Cys Gln Gln Met
    210                 215                 220

Arg Gly Arg Pro Pro Thr Phe Gly Gln Gly Thr Lys Val Glu Ile Lys
225                 230                 235                 240

Ser Ser Ser Ser Gly Ser Ser Ser Gly Ser Ser Ser Gly Ala
                245                 250                 255

Pro Thr Ser Ser Ser Thr Lys Lys Thr Gln Leu Gln Leu Glu His Leu
            260                 265                 270

Leu Leu Asp Leu Gln Met Ile Leu Asn Gly Ile Asn Asn Tyr Lys Asn
        275                 280                 285

Pro Lys Leu Thr Arg Met Leu Thr Phe Lys Phe Tyr Met Pro Lys Lys
    290                 295                 300

Ala Thr Glu Leu Lys His Leu Gln Cys Leu Glu Glu Leu Lys Pro
305                 310                 315                 320

Leu Glu Glu Val Leu Asn Leu Ala Gln Ser Lys Asn Phe His Leu Arg
                325                 330                 335

Pro Arg Asp Leu Ile Ser Asn Ile Asn Val Ile Val Leu Glu Leu Lys
```

-continued

```
                340                 345                 350
Gly Ser Glu Thr Thr Phe Met Cys Glu Tyr Ala Asp Glu Thr Ala Thr
        355                 360                 365

Ile Val Glu Phe Leu Asn Arg Trp Ile Thr Phe Cys Gln Ser Ile Ile
    370                 375                 380

Ser Thr Leu Thr Gly Asp Gly Ser Ser Gly Ser Gly Gly Ala Ser
385                 390                 395                 400

Val Arg Ser Ser Ser Arg Thr Pro Ser Asp Lys Pro Val Ala His Val
                405                 410                 415

Val Ala Asn Pro Gln Ala Glu Gly Gln Leu Gln Trp Leu Asn Arg Arg
            420                 425                 430

Ala Asn Ala Leu Leu Ala Asn Gly Val Glu Leu Arg Asp Asn Gln Leu
        435                 440                 445

Val Val Pro Ser Glu Gly Leu Tyr Leu Ile Tyr Ser Gln Val Leu Phe
    450                 455                 460

Lys Gly Gln Gly Cys Pro Ser Thr His Val Leu Leu Thr His Thr Ile
465                 470                 475                 480

Ser Arg Ile Ala Val Ser Tyr Gln Thr Lys Val Asn Leu Leu Ser Ala
                485                 490                 495

Ile Lys Ser Pro Cys Gln Arg Glu Thr Pro Glu Gly Ala Glu Ala Lys
            500                 505                 510

Pro Trp Tyr Glu Pro Ile Tyr Leu Gly Gly Val Phe Gln Leu Glu Lys
        515                 520                 525

Gly Asp Arg Leu Ser Ala Glu Ile Asn Arg Pro Asp Tyr Leu Asp Phe
    530                 535                 540

Ala Glu Ser Gly Gln Val Tyr Phe Gly Ile Ile Ala Leu
545                 550                 555

<210> SEQ ID NO 44
<211> LENGTH: 577
<212> TYPE: PRT
<213> ORGANISM: Artificial sequence
<220> FEATURE:
<223> OTHER INFORMATION: Synthetic Amino acid sequence of the
      F8-huIL2-huTNF alpha [extracellular domain] conjugate

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Glu Ile Val Leu Thr Gln Ser Pro Gly Thr Leu Ser
    130                 135                 140
```

```
Leu Ser Pro Gly Glu Arg Ala Thr Leu Ser Cys Arg Ala Ser Gln Ser
145                 150                 155                 160

Val Ser Met Pro Phe Leu Ala Trp Tyr Gln Gln Lys Pro Gly Gln Ala
            165                 170                 175

Pro Arg Leu Leu Ile Tyr Gly Ala Ser Ser Arg Ala Thr Gly Ile Pro
                180                 185                 190

Asp Arg Phe Ser Gly Ser Gly Ser Gly Thr Asp Phe Thr Leu Thr Ile
            195                 200                 205

Ser Arg Leu Glu Pro Glu Asp Phe Ala Val Tyr Tyr Cys Gln Gln Met
        210                 215                 220

Arg Gly Arg Pro Pro Thr Phe Gly Gln Gly Thr Lys Val Glu Ile Lys
225                 230                 235                 240

Ser Ser Ser Ser Gly Ser Ser Ser Gly Ser Ser Ser Gly Ala
                245                 250                 255

Pro Thr Ser Ser Ser Thr Lys Lys Thr Gln Leu Gln Leu Glu His Leu
            260                 265                 270

Leu Leu Asp Leu Gln Met Ile Leu Asn Gly Ile Asn Asn Tyr Lys Asn
        275                 280                 285

Pro Lys Leu Thr Arg Met Leu Thr Phe Lys Phe Tyr Met Pro Lys Lys
    290                 295                 300

Ala Thr Glu Leu Lys His Leu Gln Cys Leu Glu Glu Glu Leu Lys Pro
305                 310                 315                 320

Leu Glu Glu Val Leu Asn Leu Ala Gln Ser Lys Asn Phe His Leu Arg
                325                 330                 335

Pro Arg Asp Leu Ile Ser Asn Ile Asn Val Ile Val Leu Glu Leu Lys
            340                 345                 350

Gly Ser Glu Thr Thr Phe Met Cys Glu Tyr Ala Asp Glu Thr Ala Thr
        355                 360                 365

Ile Val Glu Phe Leu Asn Arg Trp Ile Thr Phe Cys Gln Ser Ile Ile
    370                 375                 380

Ser Thr Leu Thr Gly Asp Gly Ser Ser Gly Ser Gly Gly Ala Ser
385                 390                 395                 400

Gly Pro Gln Arg Glu Glu Phe Pro Arg Asp Leu Ser Leu Ile Ser Pro
                405                 410                 415

Leu Ala Gln Ala Val Arg Ser Ser Arg Thr Pro Ser Asp Lys Pro
            420                 425                 430

Val Ala His Val Val Ala Asn Pro Gln Ala Glu Gly Gln Leu Gln Trp
        435                 440                 445

Leu Asn Arg Arg Ala Asn Ala Leu Leu Ala Asn Gly Val Glu Leu Arg
    450                 455                 460

Asp Asn Gln Leu Val Val Pro Ser Glu Gly Leu Tyr Leu Ile Tyr Ser
465                 470                 475                 480

Gln Val Leu Phe Lys Gly Gln Gly Cys Pro Ser Thr His Val Leu Leu
                485                 490                 495

Thr His Thr Ile Ser Arg Ile Ala Val Ser Tyr Gln Thr Lys Val Asn
            500                 505                 510

Leu Leu Ser Ala Ile Lys Ser Pro Cys Gln Arg Glu Thr Pro Glu Gly
        515                 520                 525

Ala Glu Ala Lys Pro Trp Tyr Glu Pro Ile Tyr Leu Gly Gly Val Phe
    530                 535                 540

Gln Leu Glu Lys Gly Asp Arg Leu Ser Ala Glu Ile Asn Arg Pro Asp
545                 550                 555                 560

Tyr Leu Asp Phe Ala Glu Ser Gly Gln Val Tyr Phe Gly Ile Ile Ala
```

Leu

<210> SEQ ID NO 45
<211> LENGTH: 572
<212> TYPE: PRT
<213> ORGANISM: Artificial sequence
<220> FEATURE:
<223> OTHER INFORMATION: Synthetic Amino acid sequence of the muTNF
      alpha -F8-muIL2 conjugate

<400> SEQUENCE: 45

```
Leu Arg Ser Ser Ser Gln Asn Ser Ser Asp Lys Pro Val Ala His Val
1               5                   10                  15

Val Ala Asn His Gln Val Glu Glu Gln Leu Glu Trp Leu Ser Gln Arg
                20                  25                  30

Ala Asn Ala Leu Leu Ala Asn Gly Met Asp Leu Lys Asp Asn Gln Leu
            35                  40                  45

Val Val Pro Ala Asp Gly Leu Tyr Leu Val Tyr Ser Gln Val Leu Phe
        50                  55                  60

Lys Gly Gln Gly Cys Pro Asp Tyr Val Leu Leu Thr His Thr Val Ser
65                  70                  75                  80

Arg Phe Ala Ile Ser Tyr Gln Glu Lys Val Asn Leu Leu Ser Ala Val
                85                  90                  95

Lys Ser Pro Cys Pro Lys Asp Thr Pro Glu Gly Ala Glu Leu Lys Pro
            100                 105                 110

Trp Tyr Glu Pro Ile Tyr Leu Gly Gly Val Phe Gln Leu Glu Lys Gly
        115                 120                 125

Asp Gln Leu Ser Ala Glu Val Asn Leu Pro Lys Tyr Leu Asp Phe Ala
130                 135                 140

Glu Ser Gly Gln Val Tyr Phe Gly Val Ile Ala Leu Gly Asp Gly Ser
145                 150                 155                 160

Ser Gly Gly Ser Gly Gly Ala Ser Glu Val Gln Leu Leu Glu Ser Gly
                165                 170                 175

Gly Gly Leu Val Gln Pro Gly Gly Ser Leu Arg Leu Ser Cys Ala Ala
            180                 185                 190

Ser Gly Phe Thr Phe Ser Leu Phe Thr Met Ser Trp Val Arg Gln Ala
        195                 200                 205

Pro Gly Lys Gly Leu Glu Trp Val Ser Ala Ile Ser Gly Ser Gly Gly
210                 215                 220

Ser Thr Tyr Tyr Ala Asp Ser Val Lys Gly Arg Phe Thr Ile Ser Arg
225                 230                 235                 240

Asp Asn Ser Lys Asn Thr Leu Tyr Leu Gln Met Asn Ser Leu Arg Ala
                245                 250                 255

Glu Asp Thr Ala Val Tyr Tyr Cys Ala Lys Ser Thr His Leu Tyr Leu
            260                 265                 270

Phe Asp Tyr Trp Gly Gln Gly Thr Leu Val Thr Val Ser Ser Gly Gly
        275                 280                 285

Gly Gly Ser Gly Gly Gly Gly Ser Gly Gly Gly Gly Glu Ile Val Leu
    290                 295                 300

Thr Gln Ser Pro Gly Thr Leu Ser Leu Ser Pro Gly Glu Arg Ala Thr
305                 310                 315                 320

Leu Ser Cys Arg Ala Ser Gln Ser Val Ser Met Pro Phe Leu Ala Trp
                325                 330                 335

Tyr Gln Gln Lys Pro Gly Gln Ala Pro Arg Leu Leu Ile Tyr Gly Ala
```

```
                    340                 345                 350
Ser Ser Arg Ala Thr Gly Ile Pro Asp Arg Phe Ser Gly Ser Gly Ser
        355                 360                 365

Gly Thr Asp Phe Thr Leu Thr Ile Ser Arg Leu Glu Pro Glu Asp Phe
    370                 375                 380

Ala Val Tyr Tyr Cys Gln Gln Met Arg Gly Arg Pro Pro Thr Phe Gly
385                 390                 395                 400

Gln Gly Thr Lys Val Glu Ile Lys Ser Ser Ser Ser Gly Ser Ser Ser
                405                 410                 415

Ser Gly Ser Ser Ser Ser Gly Ala Pro Thr Ser Ser Ser Thr Ser Ser
        420                 425                 430

Ser Thr Ala Glu Ala Gln Gln Gln Gln Gln Gln Gln Gln Gln Gln Gln
        435                 440                 445

Gln His Leu Glu Gln Leu Leu Met Asp Leu Gln Glu Leu Leu Ser Arg
        450                 455                 460

Met Glu Asn Tyr Arg Asn Leu Lys Leu Pro Arg Met Leu Thr Phe Lys
465                 470                 475                 480

Phe Tyr Leu Pro Lys Gln Ala Thr Glu Leu Lys Asp Leu Gln Cys Leu
                485                 490                 495

Glu Asp Glu Leu Gly Pro Leu Arg His Val Leu Asp Leu Thr Gln Ser
                500                 505                 510

Lys Ser Phe Gln Leu Glu Asp Ala Glu Asn Phe Ile Ser Asn Ile Arg
        515                 520                 525

Val Thr Val Val Lys Leu Lys Gly Ser Asp Asn Thr Phe Glu Cys Gln
        530                 535                 540

Phe Asp Asp Glu Ser Ala Thr Val Val Asp Phe Leu Arg Arg Trp Ile
545                 550                 555                 560

Ala Phe Cys Gln Ser Ile Ile Ser Thr Ser Pro Gln
                565                 570

<210> SEQ ID NO 46
<211> LENGTH: 572
<212> TYPE: PRT
<213> ORGANISM: Artificial sequence
<220> FEATURE:
<223> OTHER INFORMATION: Synthetic Amino acid sequence of the
      F8-muIL2-muTNF alpha conjugate

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125
```

```
Gly Gly Gly Gly Glu Ile Val Leu Thr Gln Ser Pro Gly Thr Leu Ser
130                 135                 140

Leu Ser Pro Gly Glu Arg Ala Thr Leu Ser Cys Arg Ala Ser Gln Ser
145                 150                 155                 160

Val Ser Met Pro Phe Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
                180                 185                 190

Asp Arg Phe Ser Gly Ser Gly Ser Gly Thr Asp Phe Thr Leu Thr Ile
            195                 200                 205

Ser Arg Leu Glu Pro Glu Asp Phe Ala Val Tyr Tyr Cys Gln Gln Met
210                 215                 220

Arg Gly Arg Pro Pro Thr Phe Gly Gln Gly Thr Lys Val Glu Ile Lys
225                 230                 235                 240

Ser Ser Ser Ser Gly Ser Ser Ser Gly Ser Ser Ser Gly Ala
                245                 250                 255

Pro Thr Ser Ser Thr Ser Ser Thr Ala Glu Ala Gln Gln Gln
        260                 265                 270

Gln Gln Gln Gln Gln Gln Gln Gln His Leu Glu Gln Leu Leu Met
275                 280                 285

Asp Leu Gln Glu Leu Leu Ser Arg Met Glu Asn Tyr Arg Asn Leu Lys
290                 295                 300

Leu Pro Arg Met Leu Thr Phe Lys Phe Tyr Leu Pro Lys Gln Ala Thr
305                 310                 315                 320

Glu Leu Lys Asp Leu Gln Cys Leu Glu Asp Glu Leu Gly Pro Leu Arg
                325                 330                 335

His Val Leu Asp Leu Thr Gln Ser Lys Ser Phe Gln Leu Glu Asp Ala
            340                 345                 350

Glu Asn Phe Ile Ser Asn Ile Arg Val Thr Val Val Lys Leu Lys Gly
        355                 360                 365

Ser Asp Asn Thr Phe Glu Cys Gln Phe Asp Asp Glu Ser Ala Thr Val
370                 375                 380

Val Asp Phe Leu Arg Arg Trp Ile Ala Phe Cys Gln Ser Ile Ile Ser
385                 390                 395                 400

Thr Ser Pro Gln Gly Asp Gly Ser Ser Gly Ser Gly Ala Ser
                405                 410                 415

Leu Arg Ser Ser Ser Gln Asn Ser Ser Asp Lys Pro Val Ala His Val
            420                 425                 430

Val Ala Asn His Gln Val Glu Glu Gln Leu Glu Trp Leu Ser Gln Arg
        435                 440                 445

Ala Asn Ala Leu Leu Ala Asn Gly Met Asp Leu Lys Asp Asn Gln Leu
450                 455                 460

Val Val Pro Ala Asp Gly Leu Tyr Leu Val Tyr Ser Gln Val Leu Phe
465                 470                 475                 480

Lys Gly Gln Gly Cys Pro Asp Tyr Val Leu Leu Thr His Thr Val Ser
                485                 490                 495

Arg Phe Ala Ile Ser Tyr Gln Glu Lys Val Asn Leu Leu Ser Ala Val
            500                 505                 510

Lys Ser Pro Cys Pro Lys Asp Thr Pro Glu Gly Ala Glu Leu Lys Pro
        515                 520                 525

Trp Tyr Glu Pro Ile Tyr Leu Gly Gly Val Phe Gln Leu Glu Lys Gly
530                 535                 540

Asp Gln Leu Ser Ala Glu Val Asn Leu Pro Lys Tyr Leu Asp Phe Ala
```

```
                545                 550                 555                 560
            Glu Ser Gly Gln Val Tyr Phe Gly Val Ile Ala Leu
                            565                 570

<210> SEQ ID NO 47
<211> LENGTH: 411
<212> TYPE: PRT
<213> ORGANISM: Artificial sequence
<220> FEATURE:
<223> OTHER INFORMATION: Synthetic Amino acid sequence of F8-muTNF alpha
      conjugate

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Ser Met Pro Phe Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
            180                 185                 190

Asp Arg Phe Ser Gly Ser Gly Ser Gly Thr Asp Phe Thr Leu Thr Ile
        195                 200                 205

Ser Arg Leu Glu Pro Glu Asp Phe Ala Val Tyr Tyr Cys Gln Gln Met
    210                 215                 220

Arg Gly Arg Pro Pro Thr Phe Gly Gln Gly Thr Lys Val Glu Ile Lys
225                 230                 235                 240

Ser Ser Ser Ser Gly Ser Ser Ser Gly Ser Ser Ser Gly Leu
                245                 250                 255

Arg Ser Ser Ser Gln Asn Ser Ser Asp Lys Pro Val Ala His Val Val
            260                 265                 270

Ala Asn His Gln Val Glu Glu Gln Leu Glu Trp Leu Ser Gln Arg Ala
        275                 280                 285

Asn Ala Leu Leu Ala Asn Gly Met Asp Leu Lys Asp Asn Gln Leu Val
    290                 295                 300

Val Pro Ala Asp Gly Leu Tyr Leu Val Tyr Ser Gln Val Leu Phe Lys
305                 310                 315                 320

Gly Gln Gly Cys Pro Asp Tyr Val Leu Leu Thr His Thr Val Ser Arg
                325                 330                 335
```

```
Phe Ala Ile Ser Tyr Gln Glu Lys Val Asn Leu Leu Ser Ala Val Lys
            340             345             350

Ser Pro Cys Pro Lys Asp Thr Pro Glu Gly Ala Glu Leu Lys Pro Trp
        355             360             365

Tyr Glu Pro Ile Tyr Leu Gly Gly Val Phe Gln Leu Glu Lys Gly Asp
    370             375             380

Gln Leu Ser Ala Glu Val Asn Leu Pro Lys Tyr Leu Asp Phe Ala Glu
385             390             395             400

Ser Gly Gln Val Tyr Phe Gly Val Ile Ala Leu
                405             410
```

The invention claimed is:

1. A conjugate comprising interleukin-2 (IL2), tumor necrosis factor alpha (TNFα), and an antibody molecule which binds fibronectin.

2. The conjugate according to claim 1, wherein the antibody molecule is, or comprises, a single chain Fv (scFv).

3. The conjugate according to claim 1, wherein the antibody molecule binds the Extra Domain-B (ED-B) of fibronectin.

4. A conjugate comprising interleukin-2 (IL2), tumor necrosis factor alpha (TNFα), and an antibody molecule that binds the Extra Domain-A (ED-B) of fibronectin, wherein the antibody molecule comprises an antigen binding site having the complementarity determining regions (CDRs) of antibody L19 set forth in SEQ ID NOs 21-26.

5. The conjugate according to claim 4, wherein the antibody molecule comprises the VH and VL domains of antibody L19 set forth in SEQ ID Nos 27 and 28.

6. The conjugate according to claim 4, wherein the antibody molecule is an scFv, and wherein the VH domain and the VL domain of the scFv are linked by a 14 to 20 amino acid linker.

7. The conjugate according to claim 4, wherein the antibody molecule has, or comprises, the amino acid sequence of scFv L19 set forth in SEQ ID NO: 29.

8. The conjugate according to claim 4, wherein the IL2 is human IL2.

9. The conjugate according to claim 8, wherein the IL2 comprises, or consists of, the sequence set forth in SEQ ID NO: 12.

10. The conjugate according to claim 4, wherein the TNFα is human TNFα.

11. The conjugate according to claim 10, wherein the TNFα comprises, or consists of, the sequence set forth in SEQ ID NO: 15, or the sequence set forth in SEQ ID NO: 40.

12. The conjugate according to claim 4, wherein the IL2 is linked to the antibody molecule by a peptide linker.

13. The conjugate according to claim 12, wherein the peptide linker is 10 to 20 amino acids long.

14. The conjugate according to claim 4, wherein the TNFα is linked to the antibody molecule via a peptide linker.

15. The conjugate according to claim 14, wherein the peptide linker is 10 to 20 amino acids long.

16. The conjugate according to claim 4, wherein the antibody molecule is, or comprises, a single chain Fv (scFv) and, wherein the IL2 is linked to the N-terminus of the VH domain of the scFv via a peptide linker and the TNFα is linked to the C-terminus of the VL domain of the scFv via a peptide linker.

17. The conjugate according to claim 4, wherein the antibody molecule is, or comprises, a single chain Fv (scFv) and, wherein the TNFα is linked to the N-terminus of the VH domain of the scFv via a peptide linker and the IL2 is linked to the C-terminus of the VL domain of the scFv via a peptide linker.

18. The conjugate according to claim 4, wherein the antibody molecule is, or comprises, a single chain Fv (scFv) and, wherein the IL2 and the TNFα are linked to C-terminus of the VL domain of the scFv via a peptide linker.

* * * * *